United States Patent
Fukukita et al.

(10) Patent No.: US 8,444,561 B2
(45) Date of Patent: May 21, 2013

(54) ULTRASONIC DIAGNOSING APPARATUS

(75) Inventors: Hiroshi Fukukita, Tokyo (JP);
Yoshihiko Itoh, Kanagawa (JP)

(73) Assignee: Panasonic Corporation, Osaka (JP)

( * ) Notice: Subject to any disclaimer, the term of this patent is extended or adjusted under 35 U.S.C. 154(b) by 333 days.

(21) Appl. No.: 12/810,748

(22) PCT Filed: Dec. 25, 2008

(86) PCT No.: PCT/JP2008/003896
§ 371 (c)(1),
(2), (4) Date: Jun. 25, 2010

(87) PCT Pub. No.: WO2009/081569
PCT Pub. Date: Jul. 2, 2009

(65) Prior Publication Data
US 2010/0274139 A1    Oct. 28, 2010

(30) Foreign Application Priority Data

Dec. 25, 2007 (JP) .................. 2007-332082
Feb. 8, 2008 (JP) .................. 2008-028808
Feb. 25, 2008 (JP) .................. 2008-042480

(51) Int. Cl.
*A61B 8/00*    (2006.01)

(52) U.S. Cl.
USPC ..................... 600/437; 600/443; 600/459

(58) Field of Classification Search .................. 600/437, 600/443, 459
See application file for complete search history.

(56) References Cited

U.S. PATENT DOCUMENTS

| 5,642,465 | A | * | 6/1997 | Scott et al. ..................... 704/220 |
| 6,282,963 | B1 | | 9/2001 | Haider |
| 6,356,305 | B1 | * | 3/2002 | Akagawa ...................... 348/311 |
| 6,585,648 | B1 | | 7/2003 | Robinson |

| 2002/0075249 | A1 | * | 6/2002 | Kubota et al. .................. 345/204 |
| 2006/0241451 | A1 | * | 10/2006 | Nakaya et al. ................. 600/443 |
| 2007/0038091 | A1 | * | 2/2007 | Shiki ............................. 600/437 |
| 2007/0109285 | A1 | * | 5/2007 | Garverick et al. ............. 345/204 |
| 2007/0167814 | A1 | * | 7/2007 | Wakabayashi et al. ........ 600/459 |
| 2007/0195921 | A1 | * | 8/2007 | Ouchi .............................. 378/1 |

FOREIGN PATENT DOCUMENTS

| JP | 2001-187054 | 7/2001 |
| JP | 2006-506158 | 2/2006 |
| JP | 2007-68979 | 3/2007 |
| JP | 2007-244638 | 9/2007 |

* cited by examiner

*Primary Examiner* — Tse Chen
*Assistant Examiner* — Baisakhi Roy
(74) *Attorney, Agent, or Firm* — Hamre, Schumann, Mueller & Larson, P.C.

(57) ABSTRACT

An ultrasonic diagnosing apparatus includes: a transducer array 1 composed of arrayed transducer elements T1 to T6 for transmitting ultrasound; driving circuits D1A to D6A each provided for transmission channels for driving each of the transducer elements; a transmission trigger generator 2 for generating a trigger pulse for controlling each of the driving circuits; a parallel reception beam former 3 for processing reception signals from the transducer elements; a signal processor 4 for processing an output signal of the parallel reception beam former; and a control unit 5 for controlling the transmission trigger generator, the parallel reception beam former and the signal processor. The transmission trigger generator controls the width of the trigger pulse independently for each of the transmission channels to cause the driving circuit to output a driving pulse approximating a predetermined weighting value assigned to an output amplitude of each of the transmission channels in a transmission aperture of the transducer array. A circuit for forming a trapezoidal transmission beam for increasing a data acquisition rate by using parallel reception beams can be configured at low cost by using pulse amplifiers.

16 Claims, 24 Drawing Sheets

ULTRASONIC DIAGNOSING APPARATUS

TECHNICAL FIELD

The present invention relates to an ultrasonic diagnosing apparatus capable of increasing the rate at which data is acquired using a flat transmission beam and a plurality of reception beams.

BACKGROUND ART

In a conventional ultrasonic diagnosing apparatus, it has been known that the center of a spatial energy profile of an ultrasound beam is substantially flattened at the target position (see Patent document 1, for example). Thus, as shown in FIG. 38 for example, the final shape of waveform outputted from all of the transducer elements 106 is a composite waveform 107, which is determined by combining at least two predetermined component waveforms 201.

Preferably, the composite waveforms 107 of respective channels are not completely the same, and as shown in FIG. 39, they are formed as distinct component waveforms 201 corresponding to a plurality of separate ultrasound beams 202*a*, 202*b*, 202*c* . . . that are outputted substantially to all of predetermined regions over the same period. A fat TX beam 104 (hereinafter referred to as a trapezoidal transmission beam) is formed by the superimposition of these component waveforms 201.

Patent document 1: JP 2006-506158 A (paragraphs 0014, 0033, 0043, FIGS. 2, 3, 21)

DISCLOSURE OF INVENTION

Problem to be Solved by the Invention

In the conventional ultrasonic diagnosing apparatus, however, in order to form the trapezoidal transmission beam, at least two different predetermined waveforms need to be combined to obtain the final shape of waveforms outputted from the transducer elements. Consequently, high-voltage driving circuits for driving the transducer elements have to be configured using linear amplifiers, which results in high cost and also high power consumption in comparison to a case of using pulse amplifiers.

With the foregoing in mind, it is an object of the present invention to provide an ultrasonic diagnosing apparatus that allows the formation of a trapezoidal transmission beam for improving a data acquisition rate at low cost by using a plurality of parallel reception beams.

Means for Solving Problem

The ultrasonic diagnosing apparatus of the present invention includes: a transducer array composed of a plurality of arrayed transducer elements for transmitting ultrasound; a plurality of driving circuits each provided for transmission channels for driving each of the transducer elements; a transmission trigger generator for generating a trigger pulse for controlling each of the driving circuits; a parallel reception beam former for processing reception signals from the transducer elements; a signal processor for processing an output signal of the parallel reception beam former; and a control unit for controlling the transmission trigger generator, the parallel reception beam former and the signal processor. The transmission trigger generator controls a width of the trigger pulse independently for each of the transmission channels to cause the driving circuit to output a driving pulse approximating a predetermined weighting value assigned to an output amplitude of each of the transmission channels in a transmission aperture of the transducer array.

Effects of the Invention

According to the configuration described above, since it is possible to configure a circuit for forming a trapezoidal transmission beam at low cost by using pulse amplifiers, a data acquisition rate can be increased easily by using a plurality of parallel reception beams.

Figure 1:
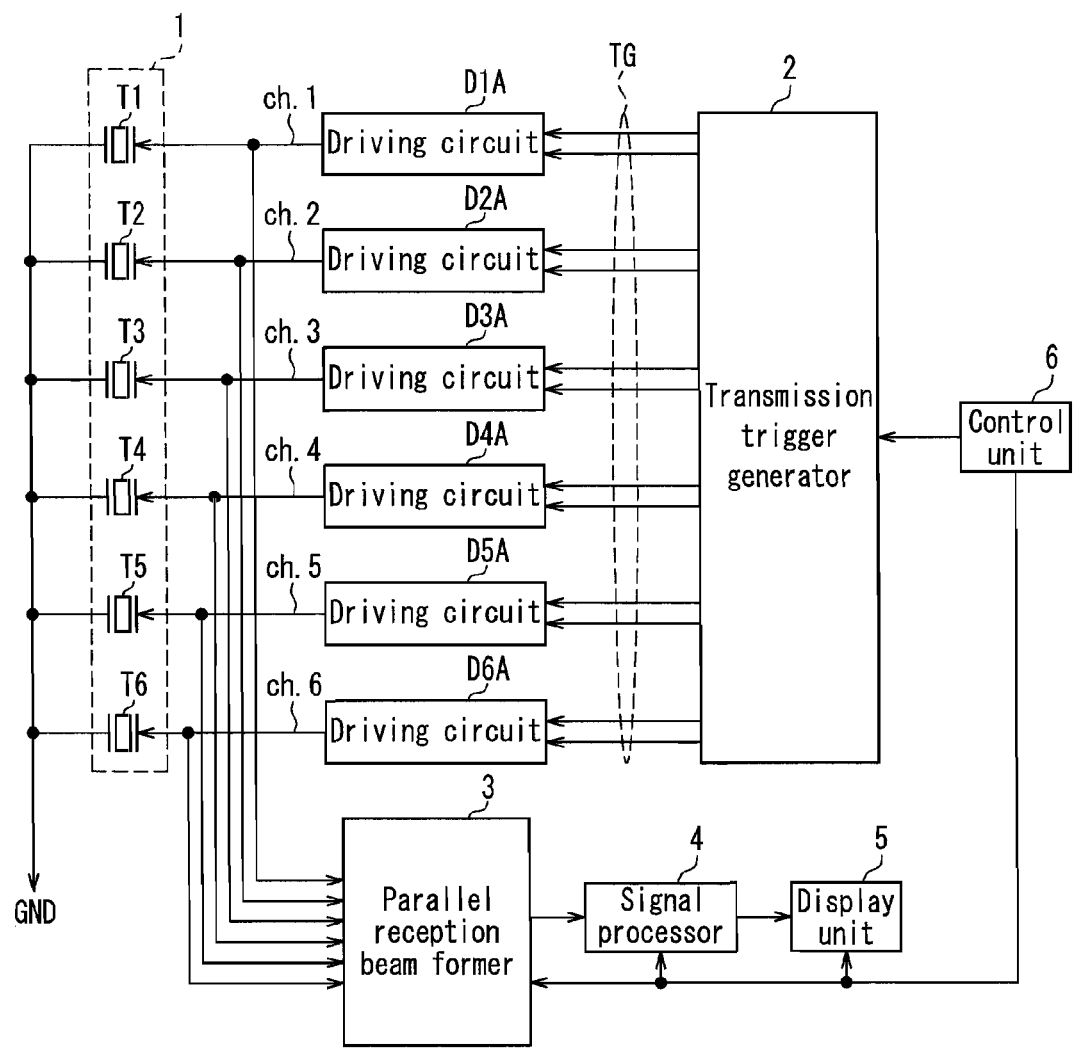
FIG. 1 is a block diagram of an ultrasonic diagnosing apparatus according to Embodiment 1 of the present invention.

DESCRIPTION OF REFERENCE NUMERALS 1 transducer array
2 transmission trigger signal generator
3 parallel reception beam former
4 signal processor
5 display unit
6 control unit
21 to 26 delay pulse generator
61 delay data generator
62 delay data compensator
63 adder
D1A to D6A, D1B to D6B driving circuit
T1-T6 transducer elements
TD1-TD6 transmission delay time
TG trigger signal group
TG1, TG1a, TG1b, TG2a, TG2b, TG3a, TG3b trigger pulse
W1a-W3a, W1b-W3b driving pulse waveform

DESCRIPTION OF THE INVENTION

Based on the configuration as mentioned above, the ultrasonic diagnosing apparatus of the present invention can be modified as follows.

That is, in comparison to the trigger pulses inputted to the driving circuits for the transmission channels corresponding to a center portion and peripheral portions of the transmission aperture of the transducer array, the trigger pulses inputted to the driving circuits for the transmission channels corresponding to intermediate areas between the center portion and the peripheral portions preferably have a narrower width. Due to this configuration, it is possible to form a trapezoidal transmission beam with more precision.

Further, the weighting to the output amplitude of each of the transmission channels may be controlled by controlling independently for each of the transmission channels the number of cycles of the trigger pulse inputted to the driving circuit. Due to this configuration, it is possible to form a trapezoidal transmission beam with more precision in a system where the number of cycles of a trigger pulse is relatively large as in the color Doppler mode.

Further, the weighting to the output amplitude of each of the transmission channels may be controlled by controlling independently for each of the transmission channels a time phase of the trigger pulse inputted to the driving circuit to be inverted.

Further, the plurality of transducer elements of the transducer array may be divided into three groups when being driven, and with respect to a time phase of the trigger pulses inputted to the driving circuits for a group at a center of the transmission aperture, a time phase of the trigger pulses inputted to the driving circuits for peripheral groups on both sides of the center group may be inverted.

Further, the driving circuits may be ternary output driving circuits, and the weighting value may be approximated by controlling independently for each of the transmission channels at least one of the width, the number of cycles and the time phase of the trigger pulse.

Further, with respect to a relative coordinate X measured from a center of the array of the transducer array as a starting point, the predetermined weighting value w (X) is assigned by the following formula.

$$w(X) = \operatorname{SIN} C(2X) + C$$

where $-1 \leq X \leq 1$ and $0.02 \leq C \leq 0.08$.

Further, the weighting value w(X) may be discretized by a quantization unit value q (where $1/8 \leq q \leq 1$).

Due to this configuration, even when controlling of a trigger pulse width becomes difficult in relatively high transmission frequencies and the accuracy of transmission weighting values drops, a trapezoidal transmission beam can be formed.

Further, when the discretized weighting value becomes 0 over a plurality of adjacent transmission channels, for some of the adjacent transmission channels where the weighting value becomes 0, the weighting value is preferably changed by the quantization unit value as a minimum unit.

Further, intervals between discretizations of the predetermined weighting value preferably are set to be longer as an ultrasound transmission frequency becomes higher.

Further, a timing of the driving pulse may be shifted by an amount of time corresponding to a ½ cycle when a polarity of the predetermined weighting value is positive and with respect to a case where the polarity is negative.

In this case, the driving circuits may be binary output driving circuits. Due to this configuration, a trapezoidal transmission beam can be formed by a simple driving circuit.

Further, time amount data corresponding to a ½ cycle may be added to or subtracted from delay data for specifying the timing of the driving pulse in accordance with the polarity of the predetermined weighting value.

Further, an output of each of the transmission channels may be controlled in accordance with an absolute weighting value corresponding to an absolute value of the predetermined weighting value.

Further, an absolute value of the predetermined weighting value may be quantized, and for some of the transmission channels where the quantized absolute weighting value becomes 0, the absolute weighting value may be changed by a minimum quantization unit.

Hereinafter, embodiments of the ultrasonic diagnosing apparatus of the present invention will be described with reference to the drawings.

Embodiment 1

FIG. 1 shows an ultrasonic diagnosing apparatus according to Embodiment 1 of the present invention. In FIG. 1, a transducer array 1 includes a plurality of arrayed transducer elements T1 to T6. The shape of the array of the transducer array 1 may be a linear array, a convex array or a matrix array where the elements are arranged in two or more dimensions. The transducer elements T1 to T6 are driven respectively by driving circuits D1A to D6A through (transmission) channels ch. 1 to ch. 6 so as to emit ultrasound beams. The driving circuits D1A to D6A are controlled by trigger pulses supplied from a transmission trigger generator 2 through a trigger signal line group TG.

A parallel reception beam former 3 receives reception signals from the transducer elements T1 to T6. An output of the parallel reception beam former 3 is subjected to signal processing by a signal processor 4 and an image corresponding to an output signal of the signal processor 4 is displayed on a display unit 5. A control unit 6 controls the transmission trigger generator 2, the parallel reception beam former 3, the signal processor 4 and the display unit 5.

The basic operation of the ultrasonic diagnosing apparatus configured as above will be described with reference to FIGS. 1 to 4C.

Figure 2:
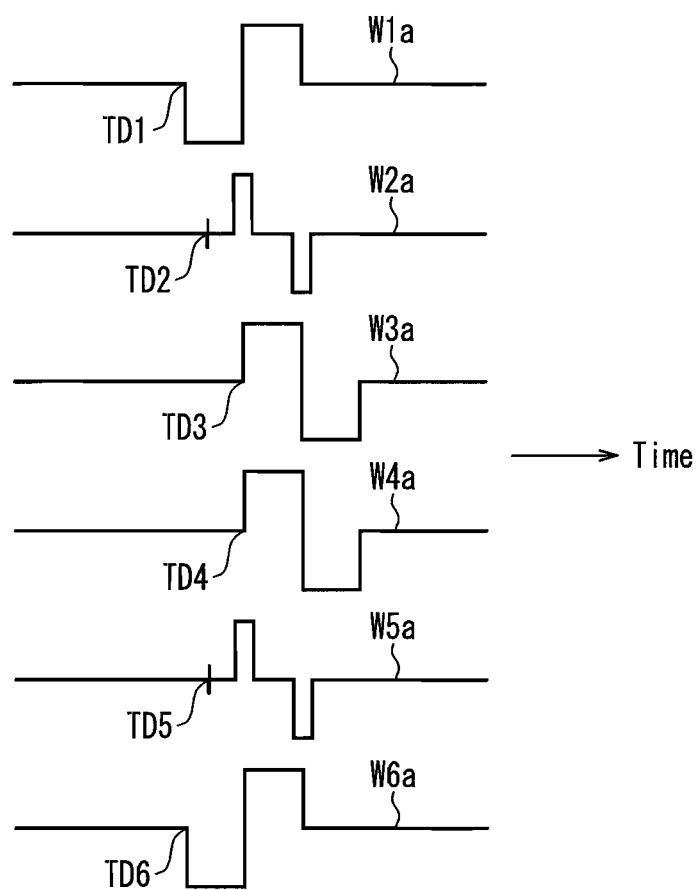
FIG. 2 is a diagram showing driving pulse waveforms outputted from driving circuits included in the ultrasonic diagnosing apparatus.

First, FIG. 2 shows waveforms of driving pulses W1a to W6a outputted from the driving circuits D1A to D6A in a state where the transducer elements T1 to T6 are removed. TD1 to TD6 assigned to the driving pulses W1a to W6a denote transmission delay times of the driving pulses W1a to W6a. Transmission beams transmitted from the transducer elements T1 to T6 can be converged by varying the transmission delay times TD1 to TD6 in a predetermined manner.

In comparison to the driving pulses W3a and W4a from channels ch. 3 and ch. 4 at the center of the transducer array 1, the driving pulses W2a and W5a from channels ch. 2 and ch. 5 located on the periphery (intermediate region) of channels ch. 3 and ch. 4 have a narrower pulse width. The driving pulses W1a and W6a from channels ch. 1 and ch. 6 located on the further periphery of channels ch. 3 and ch. 4 have a broader pulse width in comparison to the driving pulses W2a and W5a. Meanwhile, the phases of the driving pulses W1a and W6a from channels ch. 1 and ch. 6 are inverted from those of the driving pulses W2a to W5a from channels ch. 2 to ch. 5.

Figure 3:
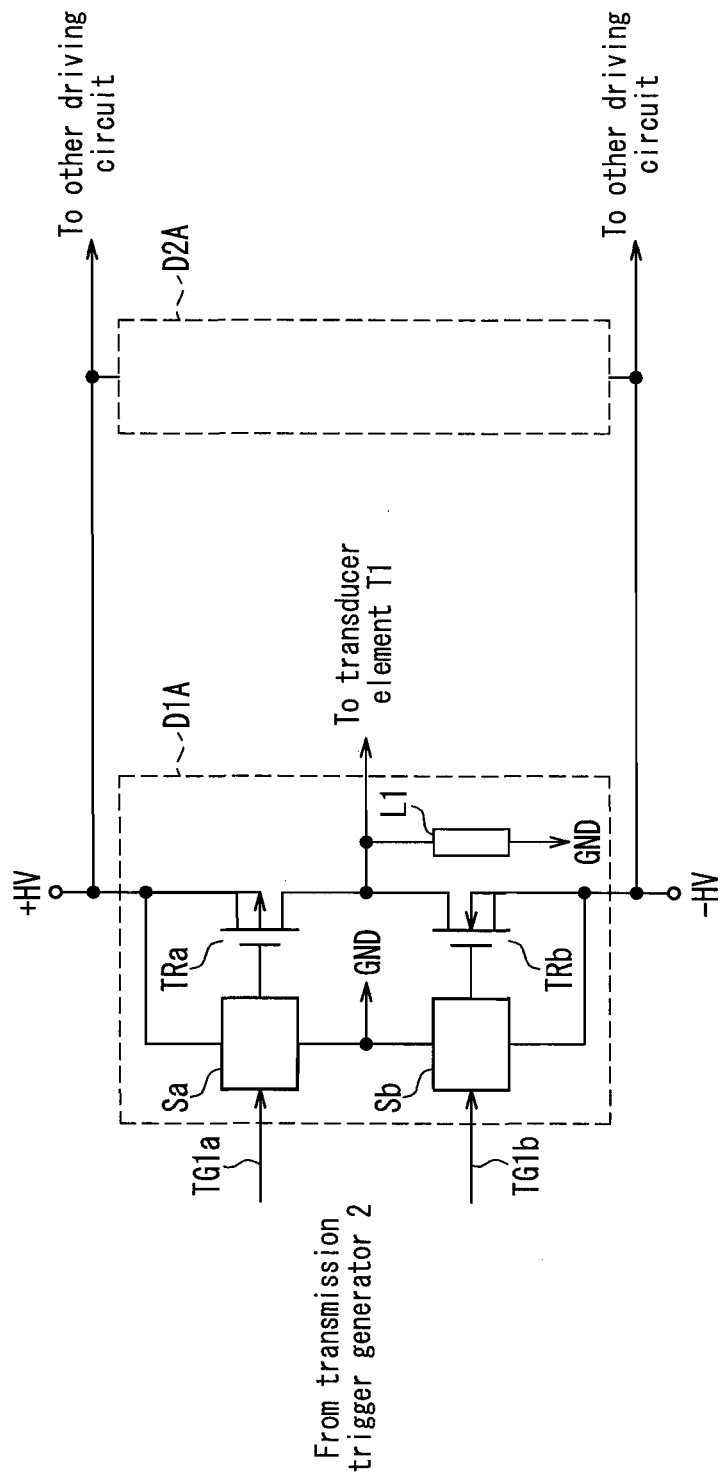
FIG. 3 is a block diagram showing a configuration of the driving circuits.

FIG. 3 shows one example of the configuration of the driving circuits D1A to D6A. Since the driving circuits D1A to D6A have the same configuration, only the configuration of the driving circuit D1A is shown in detail. The driving circuits D1A to D6A are configured to form the driving pulses W1a to W6a as described above, on the basis of trigger pulses supplied from the transmission trigger generator 2.

The driving circuit D1A includes level shifters Sa, Sb, a PMOS transistor TRa, a NMOS transistor TRb and a load L1. Two trigger signal lines of the trigger signal line group TG from the transmission trigger generator 2 are connected respectively to the level shifters Sa, Sb to supply the driving circuit D1A with trigger pulses TG1a and TG1b. One end of the level shifter Sa is connected to a positive power supply +HV and one end of the level shifter Sb is connected to a negative power supply −HV. A node between the level shifters Sa, Sb is connected to GND (ground potential).

Outputs from the level shifters Sa, Sb are inputted to the gates of the PMOS transistor TRa and the NMOS transistor TRb, respectively. The level shifters Sa, Sb shift the levels of the trigger pulses TG1a, TG1b as outputs of the low-voltage transmission trigger generator 2 so that the trigger pulses TG1a, TG1b become suitable for the high-voltage PMOS transistor TRa and NMOS transistor TRb.

The source of the PMOS transistor TRa is connected to the positive power supply +HV and the source of the NMOS transistor TRb is connected to the negative power supply −HV. The drains of the PMOS transistor TRa and the NMOS transistor TRb are connected to each other, and they are connected to the transducer element T1 as well as one end of the load L1. The other end of the load L1 is connected to GND.

Next, with reference to FIGS. 4A to 4C, a description will be given on the driving pulses W1a to W3a from the driving circuits D1A to D3A, which are based on trigger pulses supplied respectively to the driving circuits D1A to D3A.

Figure 4A:
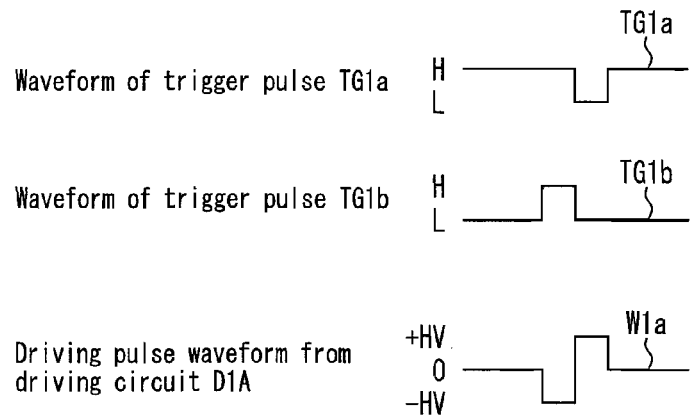
FIG. 4A is a diagram showing an example of trigger pulses inputted to the driving circuit and a driving pulse waveform outputted from the driving circuit.

FIG. 4A shows the relationship between the trigger pulses TG1a, TG1b, respectively supplied to the PMOS transistor TRa and the NMOS transistor TRb of the driving circuit D1A for generating a gate waveform, and the driving pulse W1a outputted from the driving circuit D1A.

In FIG. 4A, first, when the trigger pulse TG1b changes from L to H, the NMOS transistor TRb is turned on and the driving pulse W1a outputted from the driving circuit D1A becomes −HV. Next, when the trigger pulse TG1b changes from H to L, the NMOS transistor TRb is turned off. At the same time, since the trigger pulse TG1a changes from H to L, the PMOS transistor TRa is turned on and the driving pulse W1a outputted from the driving circuit D1A becomes +HV. Then, when the gate waveform TG1a changes from L to H, the PMOS transistor TRa is turned off and the driving pulse W1a from the driving circuit D1A becomes 0.

Figure 4B:
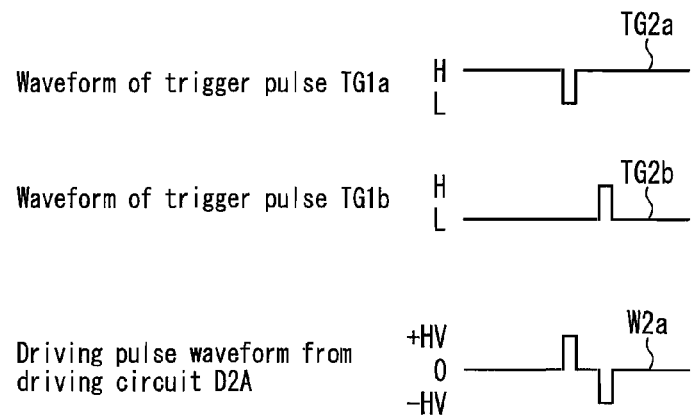
FIG. 4B is a diagram showing another example of trigger pulses inputted to the driving circuit and a driving pulse waveform outputted from the driving circuit.

FIG. 4B shows the relationship between the trigger pulses TG2a, TG2b supplied to the driving circuit D2A and the driving pulse W2a outputted from the driving circuit D2A. In FIG. 4B, first, when the trigger pulse TG2a changes from H to L, the PMOS transistor TRa is turned on and the driving pulse W2a outputted from the driving circuit D2A becomes +HV.

Next, when the trigger pulse TG2a changes from L to H, the PMOS transistor TRa is turned off and the driving pulse W2a outputted from the driving circuit D2A becomes 0. Subsequently, when the trigger pulse TG2b changes from L to H, the NMOS transistor TRb is turned on and the driving pulse W2a outputted from the driving circuit D2A becomes −HV. Next, when the trigger pulse TG2b changes from H to L, the NMOS transistor TRb is turned off and the driving pulse W2a outputted from the driving circuit D2A becomes 0.

Figure 4C:
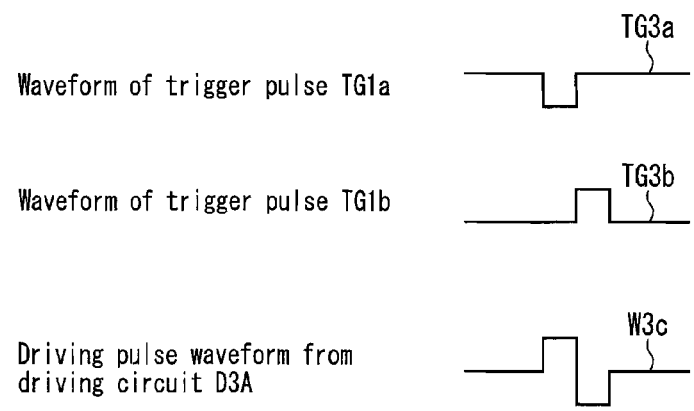
FIG. 4C is a diagram showing another example of trigger pulses inputted to the driving circuit and a driving pulse waveform outputted from the driving circuit.

FIG. 4C shows the relationship between the trigger pulses TG3a, TG3b supplied to the driving circuit D3A and the driving pulse W3a outputted from the driving circuit D3A. In FIG. 4C, first, when the trigger pulse TG3a changes from H to L, the PMOS transistor TRa is turned on and the driving pulse W3a outputted from the driving circuit D3A becomes +HV.

Next, when the trigger pulse TG3a changes from L to H, the PMOS transistor TRa is turned off. At the same time, since the trigger pulse TG3b changes from L to H, the NMOS transistor TRb is turned on and the driving pulse W3a outputted from the driving circuit D3A becomes −HV. Next, when the trigger pulse TG3b changes from H to L, the NMOS transistor TRb is turned off and the driving pulse W3a outputted from the driving circuit D3A becomes 0.

With respect to the phases of the trigger pulses TG1a, TG1b of FIG. 4A, the phases of the trigger pulses TG2a, TG2b of FIG. 4B and the trigger pulses TG3a, TG3b of FIG. 4C are inverted.

In this way, by independently controlling the width and phase of each trigger pulse for each channel, the waveforms W1a to W6a shown in FIG. 2 can be generated.

Next, hereinafter, changes in output when the above-described driving pulses W1a to W6a pass through subsystems having bandpass properties, such as the transducer elements T1 to T6, will be described. Normally, subsystems such as the parallel reception beam former 3 and the signal processor 4 also have bandpass properties.

Figure 5:
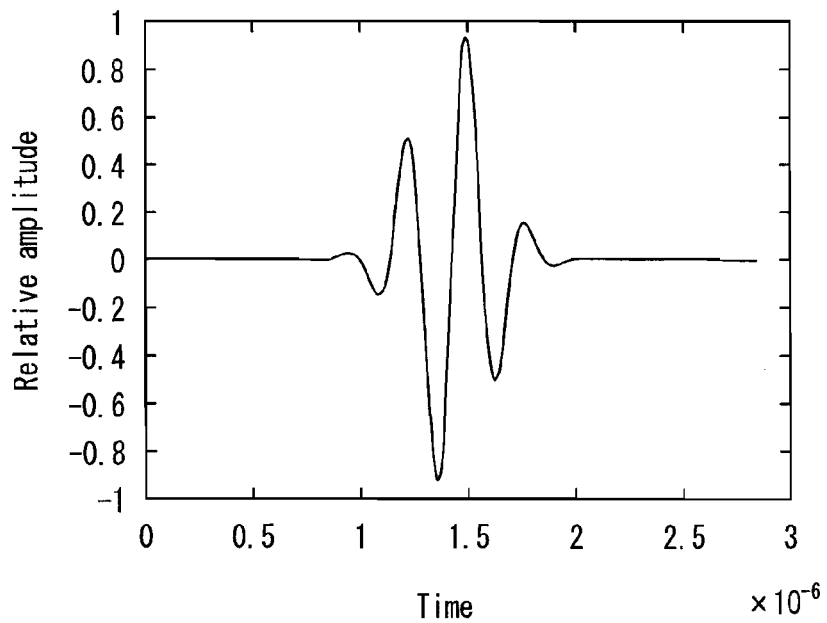
FIG. 5 is a diagram showing an example of an impulse response of a subsystem of the ultrasonic diagnosing apparatus according to Embodiment 1.

FIG. 5 shows an example of an impulse response of a subsystem having bandpass properties with a fractional bandwidth of 0.6. Outputs from the subsystem having such an impulse response are simulated by applying driving pulses of various waveforms to the system.

Figure 6A:
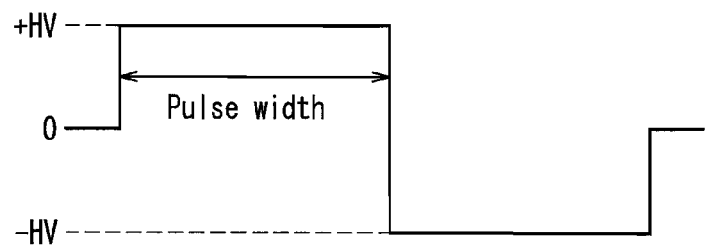
FIG. 6A is a diagram showing an example of a driving pulse waveform of the ultrasonic diagnosing apparatus.
Figure 6B:
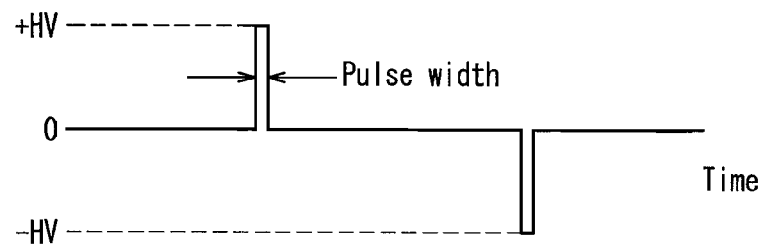
FIG. 6B is a diagram showing an example of a driving pulse waveform of the ultrasonic diagnosing apparatus.
Figure 7:
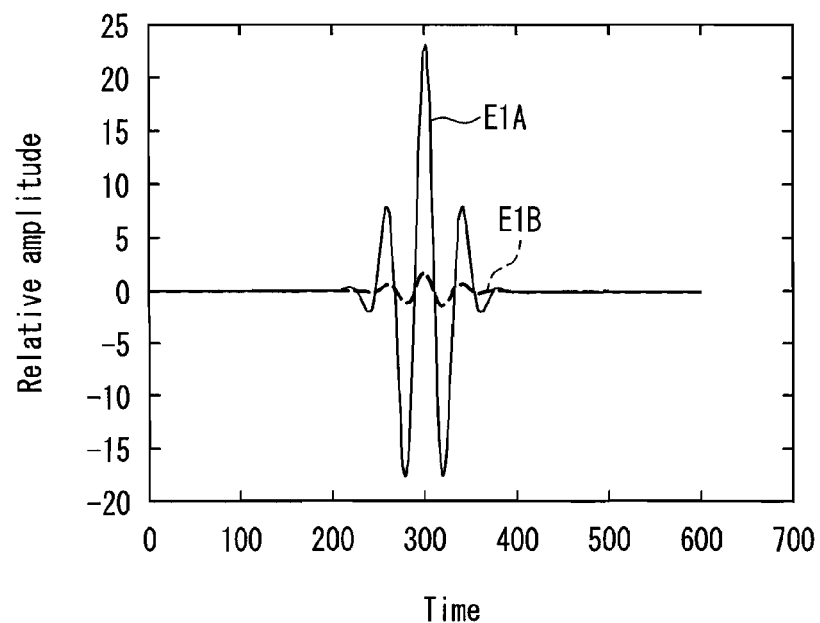
FIG. 7 is a diagram showing an example of output waveforms of a subsystem of the ultrasonic diagnosing system.

First, the simulation results on an example of the driving pulses shown in FIGS. 6A to 6B will be described. The width of the driving pulse of FIG. 6B is ½₁ of the width of the driving pulse of FIG. 6A. FIG. 7 shows outputs from the subsystem in this case. In FIG. 7, an output waveform E1A indicated by a solid line corresponds to the driving pulse of FIG. 6A and an output waveform E1B indicated by a broken line corresponds to the driving pulse of FIG. 6B. The amplitude of the output waveform E1B is about 1/12 of the amplitude of the output waveform E1A.

Figure 8A:
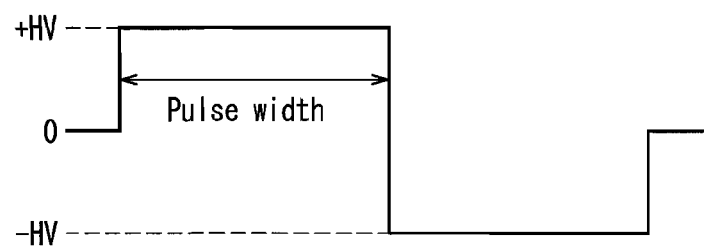
FIG. 8A is a diagram showing an example of a driving pulse waveform of the ultrasonic diagnosing apparatus.
Figure 8B:
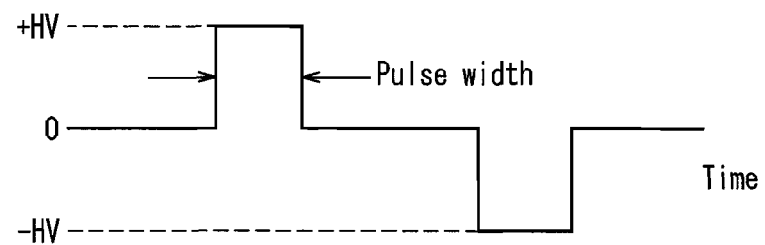
FIG. 8B is a diagram showing an example of a driving pulse waveform of the ultrasonic diagnosing apparatus.
Figure 9:
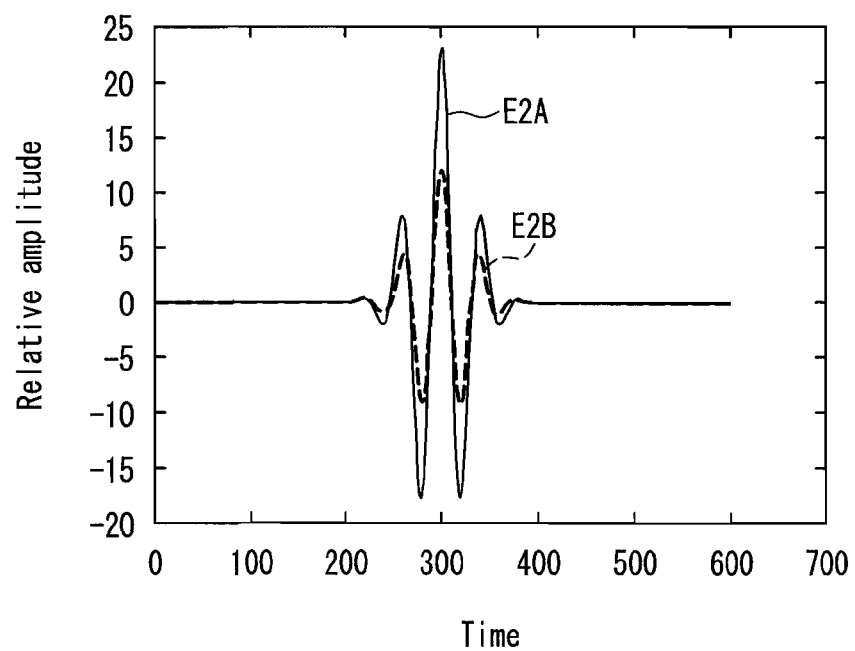
FIG. 9 is a diagram showing an example of output waveforms of a subsystem of the ultrasonic diagnosing system.

Next, the simulation results on an example of the driving pulses shown in FIGS. 8A to 8B will be described. The width of the driving pulse of FIG. 8B is ⅓ of the width of the driving pulse of FIG. 8A. FIG. 9 shows outputs from the subsystem in this case. In FIG. 9, an output waveform E2A indicated by a solid line corresponds to the driving pulse of FIG. 8A and an output waveform E2B indicated by a broken line corresponds to the driving pulse of FIG. 8B. The amplitude of the output waveform E2B is about ½ of the amplitude of the output waveform E2A. In this way, by varying pulse widths, the output amplitude of the subsystem can be controlled.

Figure 10:
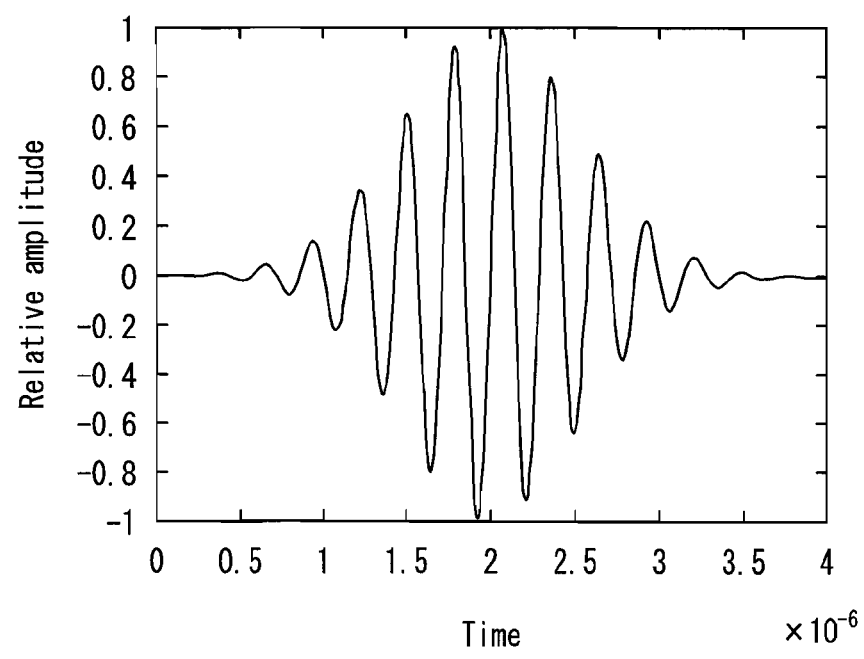
FIG. 10 is a diagram showing an example of an impulse response of a subsystem of the ultrasonic diagnosing apparatus.
Figure 11A:
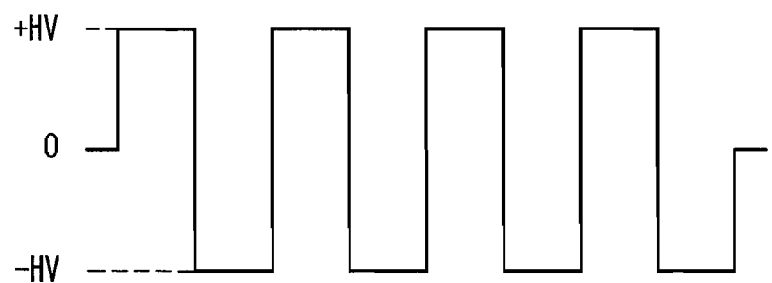
FIG. 11A is a diagram showing an example of a driving pulse waveform of the ultrasonic diagnosing apparatus.
Figure 11B:
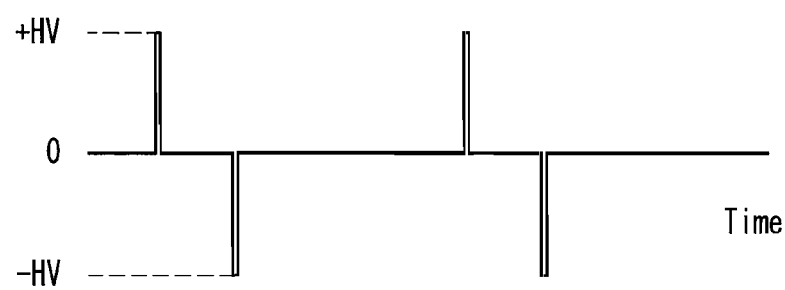
FIG. 11B is a diagram showing an example of a driving pulse waveform of the ultrasonic diagnosing apparatus.

Next, FIG. 10 shows an example of an impulse response of a subsystem with a fractional bandwidth of 0.2. A description will be given for a case where driving pulses shown in FIGS. 11A and 11B are applied to the subsystem with such an impulse response. The width of the driving pulse of FIG. 11B is ½₁ of the width of the driving pulse of FIG. 11A. Further, the number of cycles of the driving pulse of FIG. 11B is 2 and the number of cycles of the driving pulse of FIG. 11A is 4.

Figure 12:
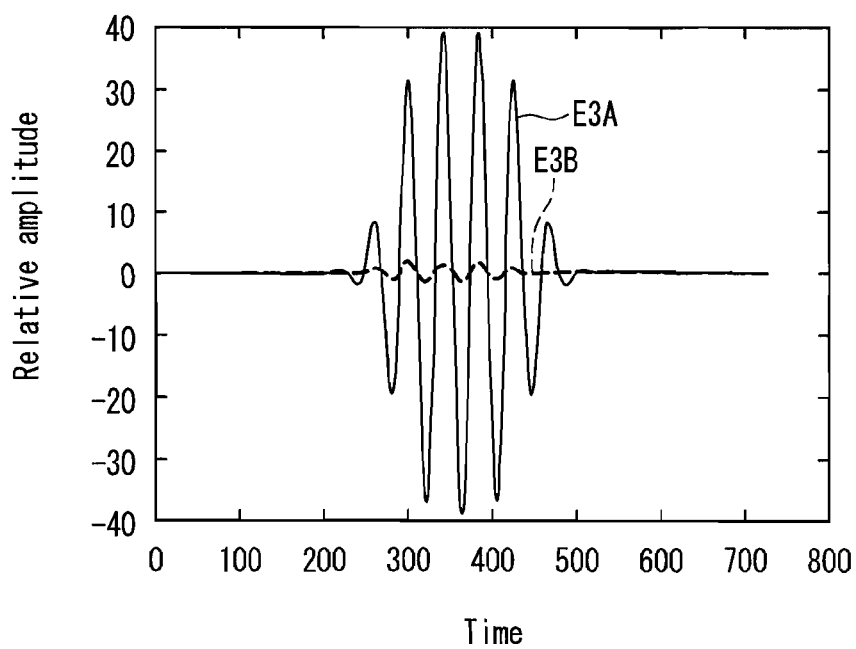
FIG. 12 is a diagram showing an example of output waveforms of a subsystem of the ultrasonic diagnosing apparatus.

FIG. 12 shows outputs from the subsystem in this case. In FIG. 12, an output waveform E3A indicated by a solid line corresponds to the driving pulse of FIG. 11A and an output waveform E3B indicated by a broken line corresponds to the driving pulse of FIG. 11B. The amplitude of the output waveform E3B is about 1/25 of the amplitude of the output waveform E3A.

When the signal processor 4 has a narrow fractional bandwidth such as in the color Doppler mode, it is possible to change the output amplitude of the subsystem more finely by varying the number of cycles of the trigger pulses as in the above case.

Next, by taking the transducer array 1 as an example, a description will be given on the output amplitude of each of the transducer elements T1, T2, . . . and the horizontal distribution of relative sound pressure level of a transmission beam on the focal plane of the beam (hereinafter referred to as a beam shape). A predetermined weighting value is set on the output amplitude of each channel in a transmission aperture of the transducer array 1. It has been well known that the beam shape is expressed by Fourier transform of a distribution of weighting values assigned to the output amplitudes of respective channels in the transmission aperture (hereinafter referred to as "transmission aperture weighting values") or conversely the transmission aperture weighting values can be expressed by inverse Fourier transform of the beam shape. For this reason, to obtain a rectangular beam shape, each transmission aperture weighting value wo(X) is set as shown by Formula (1) and an output of a transducer element is made proportional to this weighting value wo(X).

$$wo(X) = \sin(2\pi X)/2\pi X \quad (1)$$

where X denotes a relative coordinate of the transducer element measured from the center of the transducer array 1.

However, Formula (1) is not zero in the infinite range of X. Therefore, in order to deal with the fact that the size of the transducer array 1 is limited, it is necessary to limit the value range of X. On the other hand, limiting the value of X makes the beam shape unrectangular. Thus, in the present embodiment, each transmission aperture weighting value w(X) is set as shown by the following formula.

$$w(X) = \text{SIN } C(2X) + C \quad (2)$$

where SIN C(2X)=sin(2πX)/2πX
X=x/a
x denotes a positional coordinate of each transducer element of the transducer array and 2a denotes the maximum width of the transducer array. Thus, $$-1 \leq X \leq 1 \quad (3)$$

and the constant C is set as $$0.02 \leq C \leq 0.08 \quad (4).$$

Figure 13:
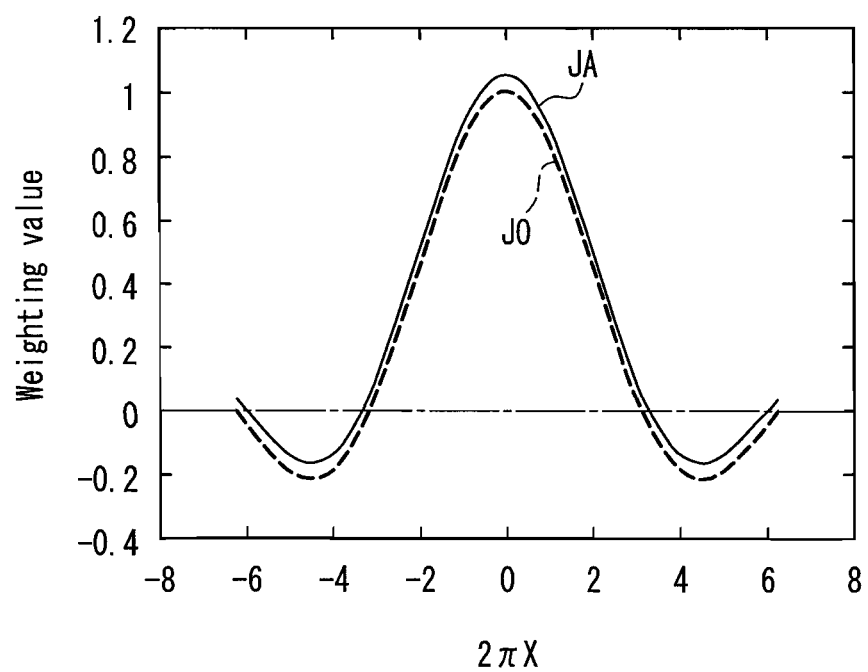
FIG. 13 is an example of weighting values of the ultrasonic diagnosing apparatus.
Figure 14A:
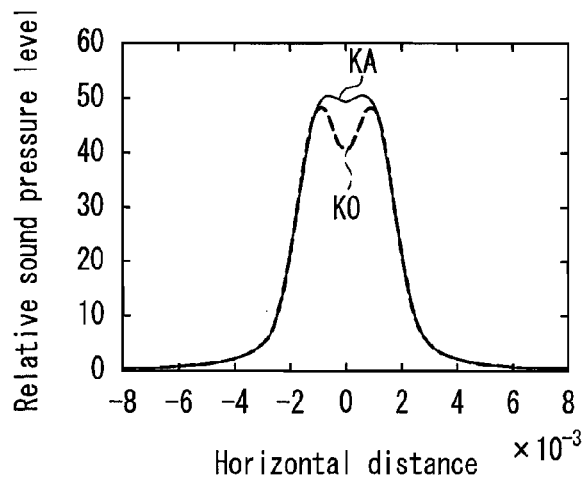
FIG. 14A is a diagram showing an example of beam shapes of the ultrasonic diagnosing apparatus.

FIG. 13 shows an example of transmission aperture weighting values assigned to a transmission aperture with 96 channels where −1≤X≤1. A broken line J0 indicates a case of Formula (1), in other words, a case where C=0 in Formula (2) and a solid line JA indicates a case where C=0.05 in Formula (2). FIG. 14A shows beam shapes on the transmission focal plane of the transducer array, and each beam shape corresponds to each set of the transmission aperture weighting values shown in FIG. 13. A broken line K0 corresponds to the broken line J0 in FIG. 13 and a solid line KA corresponds to the solid line JA in FIG. 13. As is clear from FIG. 14A, a beam shape closer to a trapezoid is obtained in the case indicted by the solid line KA where C=0.05, which beam shape is suited for parallel reception.

Figure 14B:
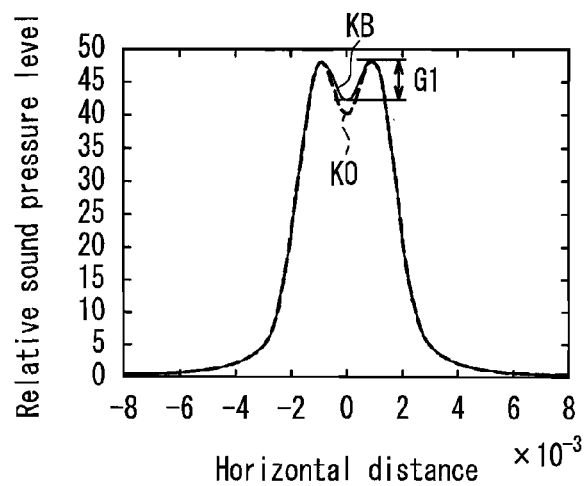
FIG. 14B is a diagram showing an example of beam shapes of the ultrasonic diagnosing apparatus.
Figure 14C:
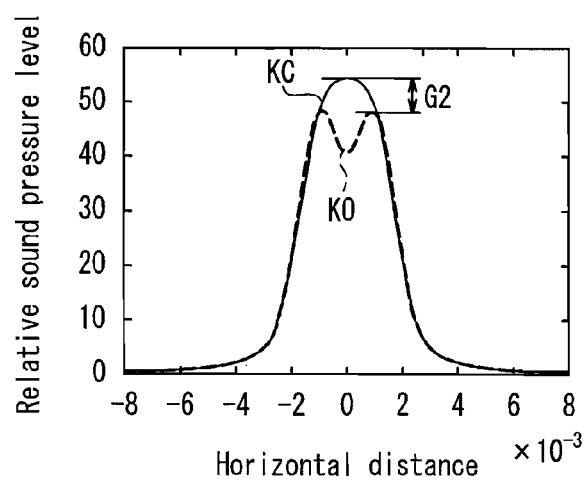
FIG. 14C is a diagram showing an example of beam shapes of the ultrasonic diagnosing apparatus.

A solid line KB in FIG. 14B indicates a beam shape in a case where C=0.02 and a solid line KC in FIG. 14C indicates a beam shape in a case where C=0.08. In comparison to a reduction in relative sound pressure level at the center of the beam (indicated by the broken line K0) that occurs in the case of Formula (1), in other words, when C=0 in Formula (2), the amount of reduction in relative sound pressure level G1 in FIG. 14B is smaller and also the amount of increase in the level G2 in FIG. 14C is much smaller, meaning that a desirable beam shape is obtained.

FIGS. 15 to 18 show effects of transmission aperture weighting. The drawings show results on a comparison between a case without weighting where the amplitude of each channel is uniform and a case with weighting in Formula (2).

Figure 15:
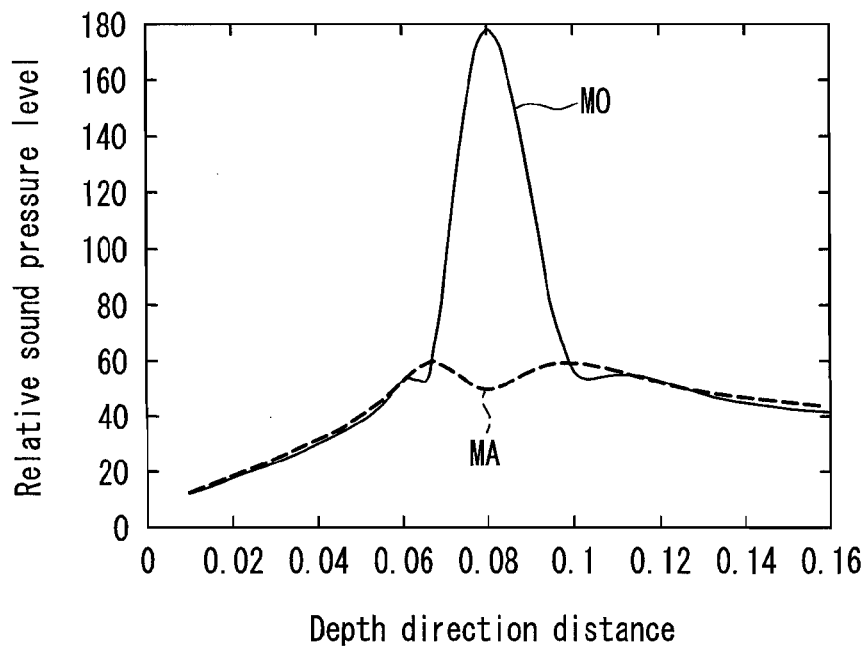
FIG. 15 is a diagram showing an example of depth direction dependency of relative sound pressure level of the ultrasonic diagnosing apparatus.
Figure 16:
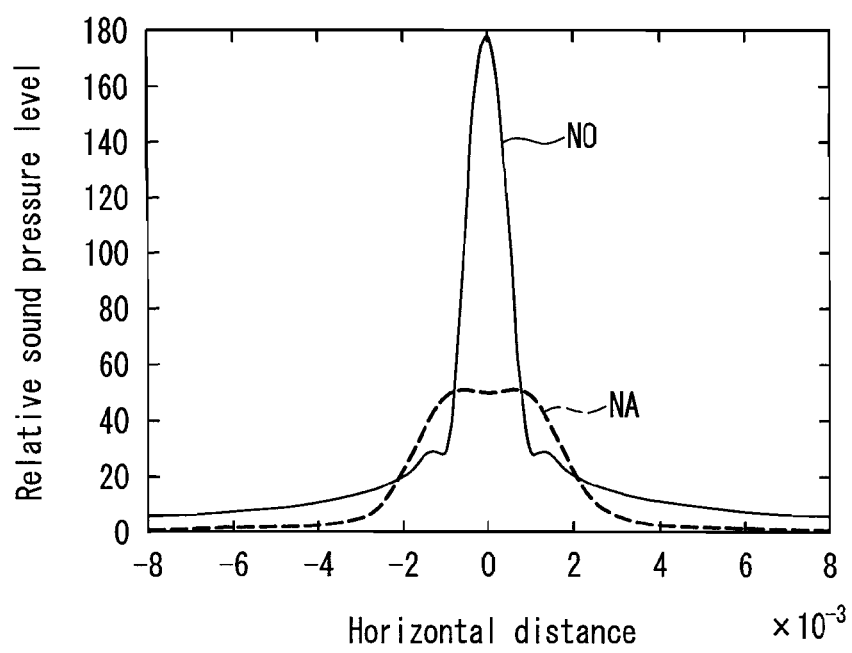
FIG. 16 is a diagram showing an example of beam shapes of the ultrasonic diagnosing apparatus.

FIG. 15 is a diagram showing the depth dependence of the relative sound pressure level at the center of a transmission beam. A solid line M0 indicates the case without weighting where the amplitude of each channel is uniform and a broken line MA indicates the case with weighting in Formula (2). In comparison to the relative sound pressure level in the case without weighting indicated by the solid line M0, the relative sound pressure level in the case with weighting indicted by the broken line MA has less depth dependence and the sound pressure does not increase rapidly at the focal point. As a result, a desirable state of the beam shape with less variation over a wide depth range is obtained. FIG. 16 shows beam shapes on the transmission focal plane. In comparison to the case without weighting indicated by a solid line N0, the beam is thicker and has a trapezoidal shape in the case with weighting indicated by a broken line NA.

Figure 17:
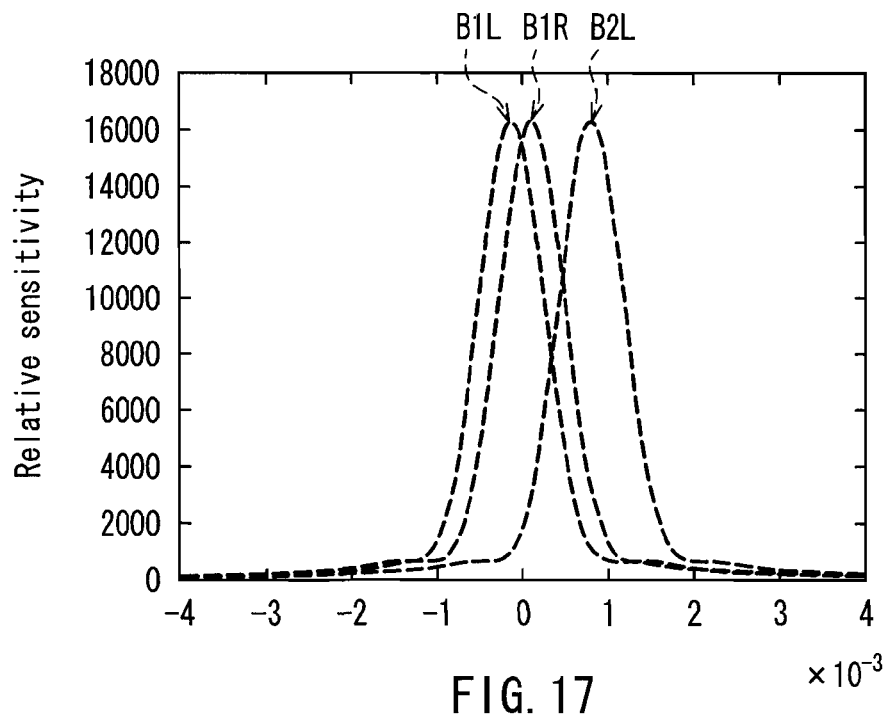
FIG. 17 is a diagram showing relative sensitivity of transmission-reception directivity of two parallel reception in a conventional ultrasonic diagnosing apparatus where weighting values are uniform.

FIG. 17 shows the relative sensitivity of transmission-reception directivity of two parallel reception in the case without weighting. The intervals between transmission-reception directionality B1L (the left side of the drawing) and B1R (the right side of the drawing) corresponding to a first transmission beam and transmission-reception directionality B2L corresponding to a second transmission beam are not even. This results in such problems as the development of a lattice pattern on a tomogram to be obtained.

Figure 18:
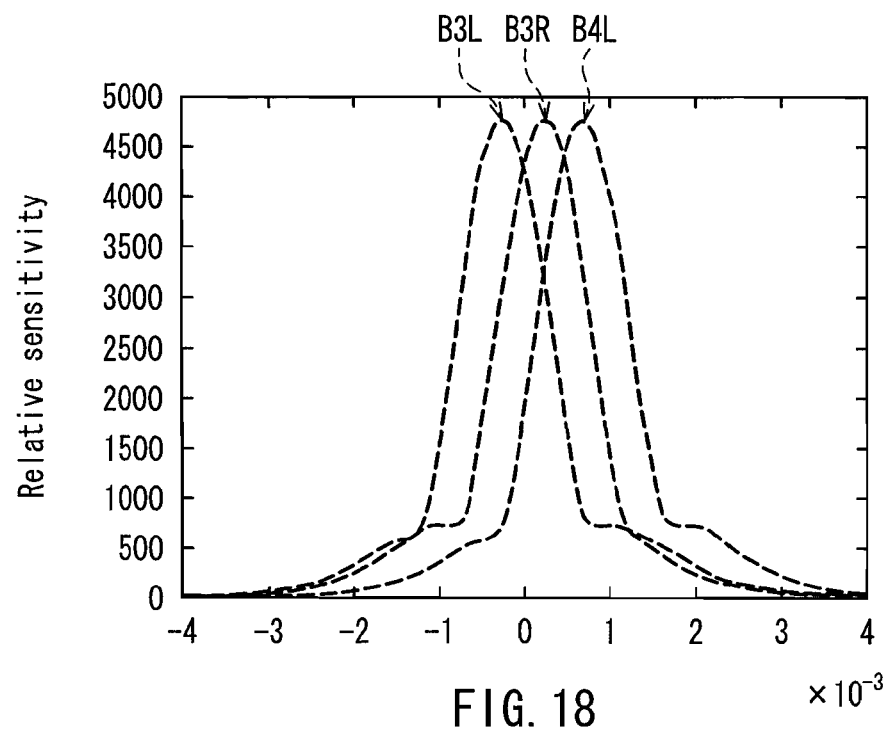
FIG. 18 is a diagram showing relative sensitivity of transmission-reception directivity of two parallel reception in the ultrasonic diagnosing apparatus according to Embodiment 1 of the present invention.

FIG. 18 shows the transmission-reception directionality of two parallel reception in the case with weighting in Formula (2). The intervals between transmission-reception directionality B3L (the left side of the drawing) and B3R (the right side of the drawing) corresponding to a third transmission beam and transmission-reception directionality B4L corresponding to a fourth transmission beam are even. As a result, the development of a lattice pattern on a tomogram to be obtained is reduced significantly. It is desirable, in performing parallel reception, to carry out such weighting to achieve a wide and trapezoidal beam shape that varies less throughout a wide depth range.

Next, the influences of quantizing weighting values by a quantization unit value q will be described with reference to FIGS. 19 to 22. A quantized weighting value is set on the basis of Formula (5).

$$wq(x) = \text{round}(w(x)/\times q \quad (5)$$

where the function round ( ) means that variables in the parentheses are rounded off.

Figure 19:
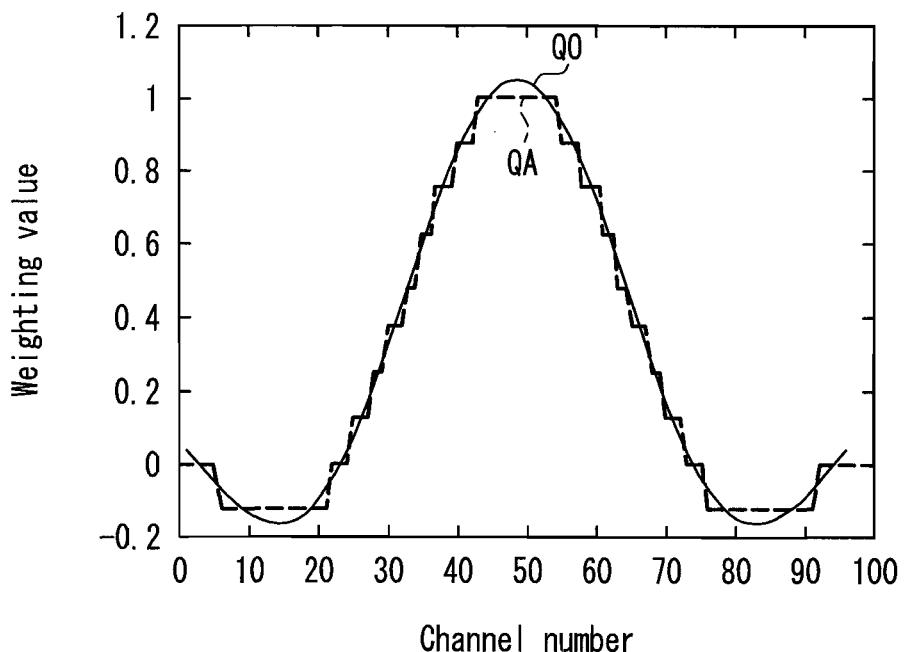
FIG. 19 is a diagram showing an example in the ultrasonic diagnosing apparatus where weighting values are quantized.

With regard to an aperture with 96 channels, a solid line Q0 in FIG. 19 indicates weighting values when each weighting value of Formula (2) is not quantized and a broken line QA indicates weighting values when the quantization unit value $q=\frac{1}{8}$.

Figure 20:
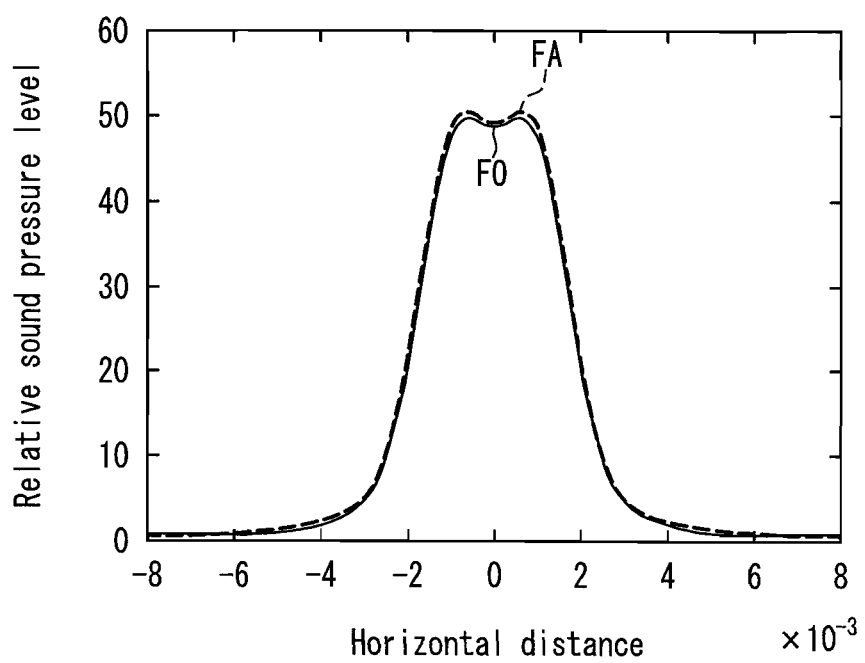
FIG. 20 is a diagram showing a beam shape in the ultrasonic diagnosing apparatus in a case of weighting values in FIG. 19.

FIG. 20 shows beam shapes corresponding to FIG. 19. A solid line F0 indicates the case without quantization indicated by the solid line Q0 in FIG. 19 and a broken line FA indicates the case with quantization indicated by the broken line QA in FIG. 19. There is nearly no difference between the case without quantization indicated by the solid line F0 and the case with quantization indicated by the broken line FA.

To achieve the transmission aperture weighting values shown in FIG. 19, the following may be performed. First, the trigger pulses are set such that their width is wide at the center of the aperture of the transducer array, becomes narrow towards the peripheral portions of the aperture and becomes wide again in the further peripheral portions where weighting values become negative. Further, transducers of the transducer array to be driven are divided into three groups. The phases of trigger pulses inputted to the driving circuits for driving the transducers in the group at the center of the transmission aperture are set as a state A and the phases of trigger pulses inputted to the driving circuits for driving transducers in the peripheral groups adjacent to the group at the center and where the weighting values are negative are set as a state B, and the phases of the trigger pulses in the state A whereby the phases of the trigger pulses in the state B are inverted from each other.

Figure 21:
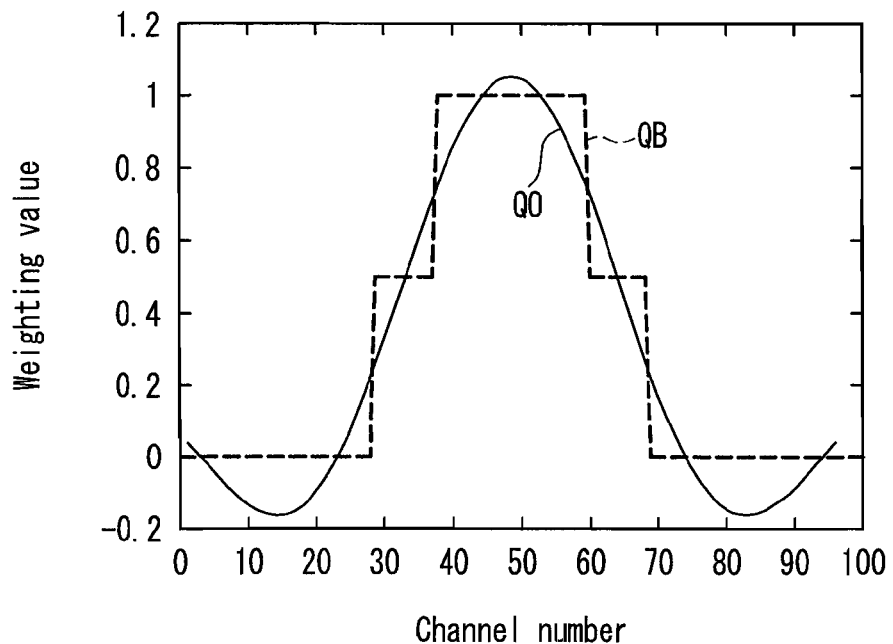
FIG. 21 is a diagram showing an example in the ultrasonic diagnosing apparatus where weighting values are quantized.
Figure 22:
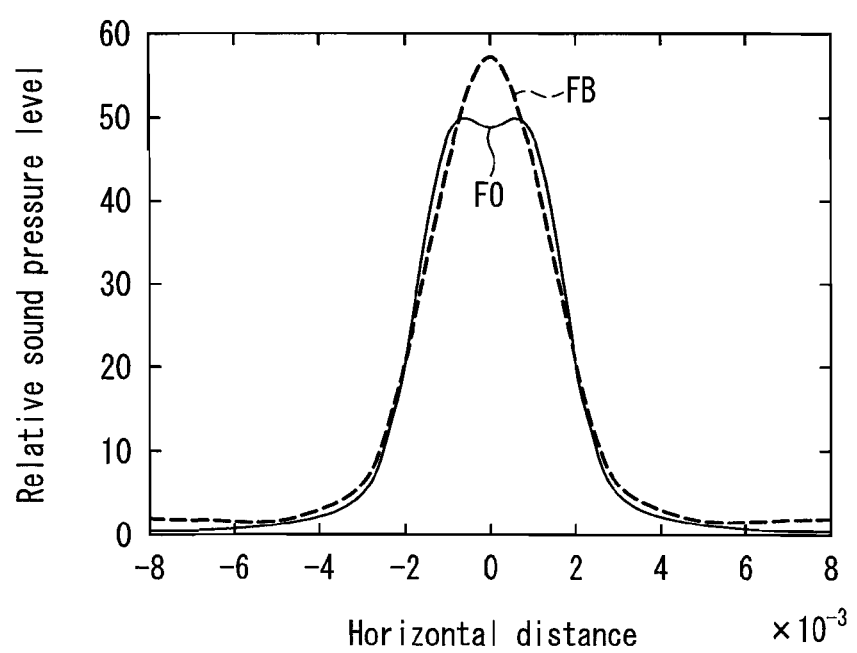
FIG. 22 is a diagram showing a beam shape in the ultrasonic diagnosing apparatus in a case of weighting values in FIG. 21.

A broken line QB in FIG. 21 indicates weighting values in a case where q=0.5 in Formula (5). Weighting values of a plurality of channels in which they are negative are rounded off to 0. A broken line FB in FIG. 22 indicates a transmission beam shape obtained by using the quantized weighting values indicated by the broken line QB in FIG. 21, where a trapezoidal transmission beam shape is not obtained.

Figure 23:
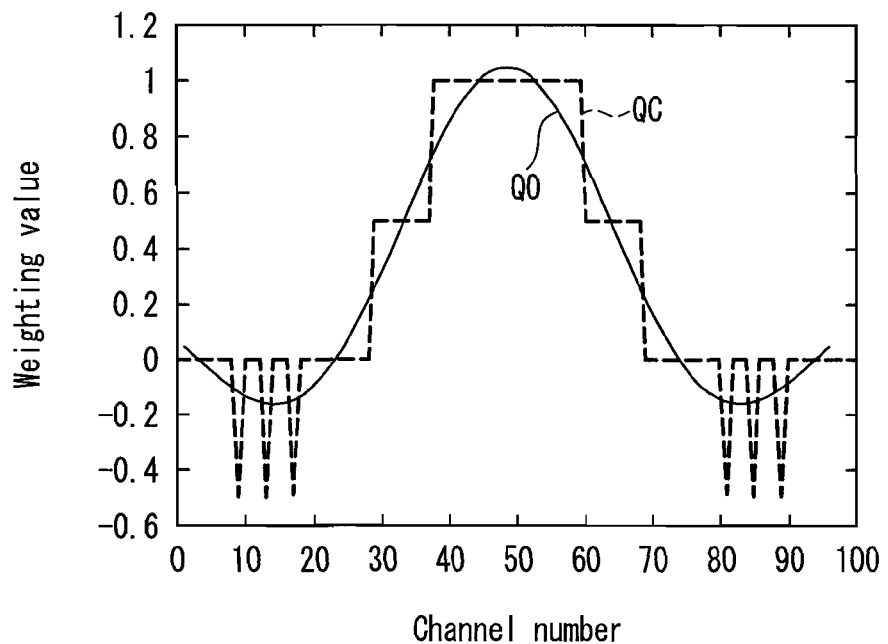
FIG. 23 is a diagram showing an example in the ultrasonic diagnosing apparatus where weighting values are quantized.
Figure 24:
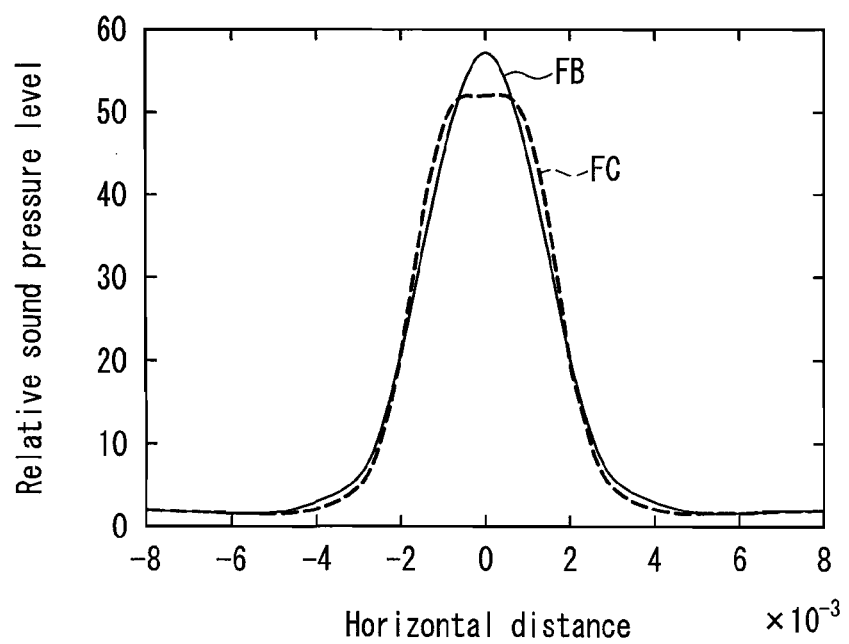
FIG. 24 is a diagram showing a beam shape in the ultrasonic diagnosing apparatus in a case of weighting values in FIG. 23.

A broken line QC in FIG. 23 indicates weighting values in a case where q=0.5 in Formula (5) and further the weighting values at channels 9, 13, 17, 81, 85 and 89 are changed to −0.5 on the basis of a minimum quantization value. A broken line FC in FIG. 24 indicates a transmission beam shape obtained by using the weighting values indicated by the broken line QC in FIG. 23, where a trapezoidal transmission beam shape is obtained.

In this way, when the transmission weighting values of the transducer array are discretized and the discrete weight values become 0 over a plurality of adjacent channels, for some of the adjacent channels where the weighting values become 0, the weighting values are changed by the minimum quantization value. As a result, a trapezoidal beam shape can be obtained. The weighting values indicated by the broken line QC in FIG. 23 are +1, +0.5, 0 and −0.5 (phase inversion) and they can be approximated by using the driving pulse waveforms shown in FIGS. 8A and 8B.

Figure 25:
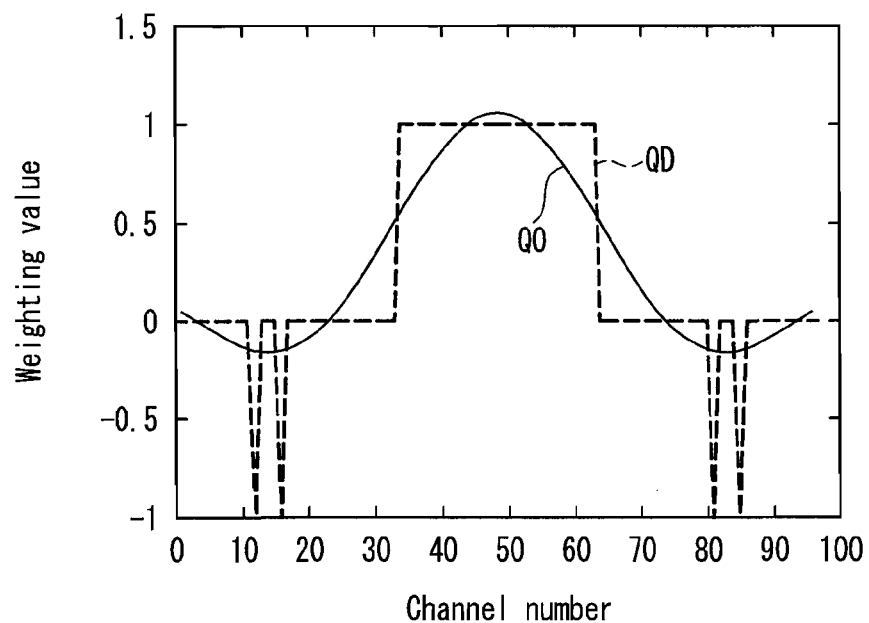
FIG. 25 is a diagram showing an example in the ultrasonic diagnosing apparatus where weighting values are quantized.
Figure 26:
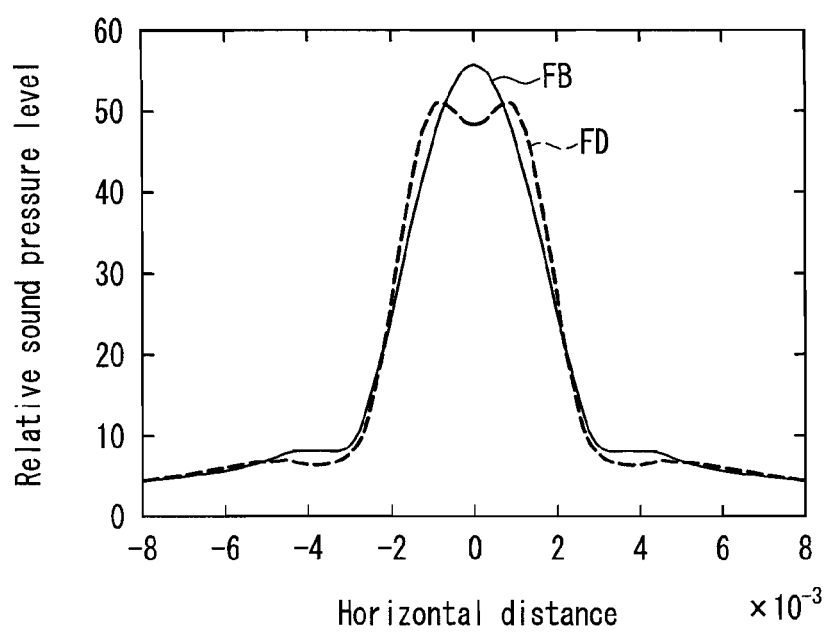
FIG. 26 is a diagram showing a beam shape in the ultrasonic diagnosing apparatus in a case of weighting values in FIG. 25.

The broken line QD in FIG. 25 indicates weighting values in a case where q=1 in Formula (5) and the weighting values at channels 12, 16, 81 and 85 are set to −1. A broken line FD in FIG. 26 indicates a transmission beam shape obtained by using the weighting values indicated by the broken line QD in FIG. 25, where a trapezoidal beam shape is obtained. The weighting values indicated by the broken line QD in FIG. 25 can be achieved by a ternary driving circuit whose output has states of 1, 0 and −1 (phase inversion).

As described above, in the case where the absolute maximum value of the weighting values is about 1 as in Formula (2), by setting the quantization unit value q of the weighting values to satisfy $\frac{1}{8} \leq q \leq 1$ and changing the weighting values by the quantization minimum value for some of the adjacent channels where the weight values quantized by the quantization unit value q become 0, a trapezoidal beam shape can be obtained. Further, at high frequencies, it is difficult to obtain a driving pulse with a narrow pulse width and it also is difficult to reduce the quantization unit value q. Thus, it is preferable to increase intervals between discretizations of transmission weighting values as the transmission frequency becomes higher.

As described above, according to the ultrasonic diagnosing apparatus of the present embodiment, it is possible to form a trapezoidal transmission beam by independently controlling, for each transmission channel, the width of each trigger pulse inputted to each driving circuit for the transducer array so as to approximate transmission weighting values of the transducer array. As a result, a rate at which data is acquired can be increased easily by using a plurality of reception beams.

Embodiment 2

Figure 27:
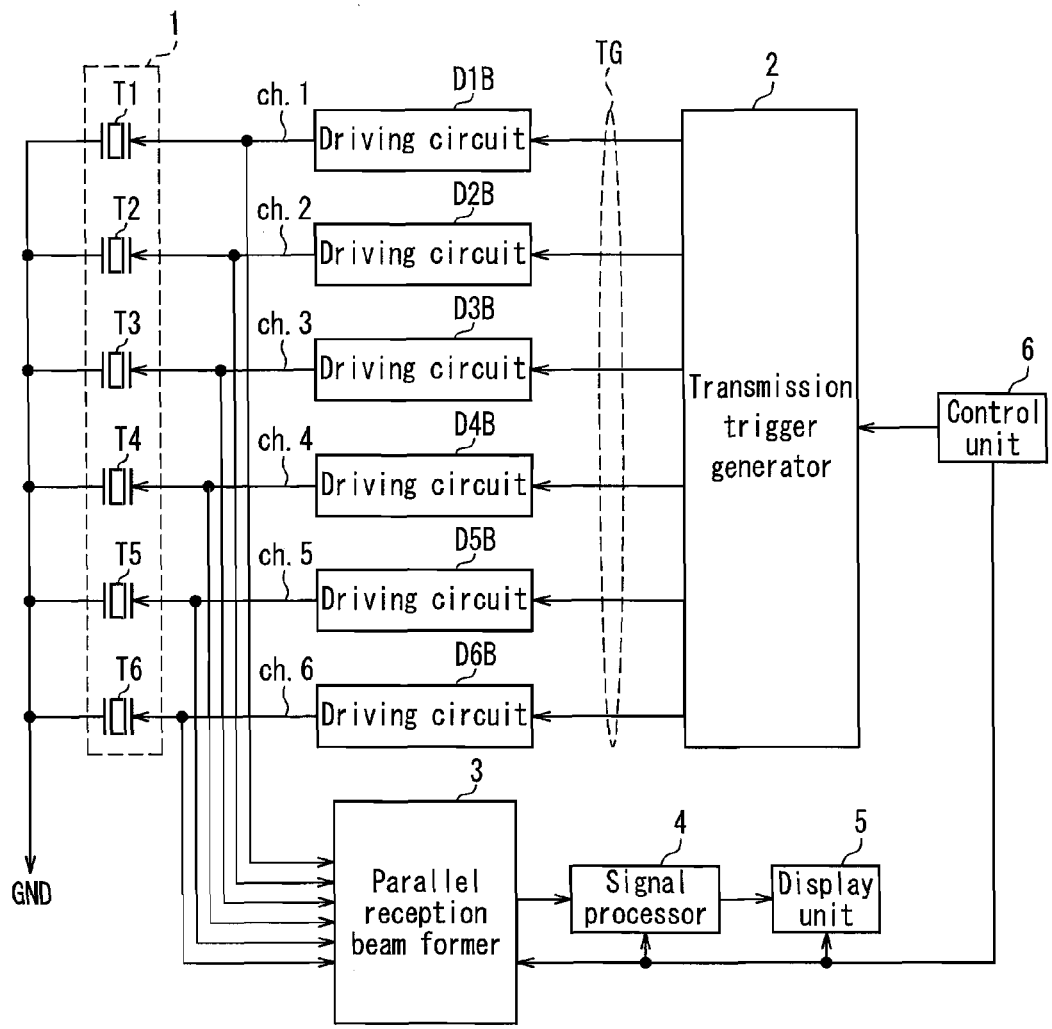
FIG. 27 is a block diagram of an ultrasonic diagnosing apparatus according to Embodiment 2 of the present invention.

FIG. 27 shows an ultrasonic diagnosing apparatus according to Embodiment 2 of the present invention. Basically, the ultrasonic diagnosing apparatus according to the present embodiment has a configuration similar to that of the ultrasonic diagnosing apparatus according to Embodiment 1 shown in FIG. 1. Thus, components similar to those of the apparatus of FIG. 1 are denoted by the same reference numerals and the descriptions thereof will not be repeated.

The ultrasonic diagnosing apparatus according to the present embodiment is different from the ultrasonic diagnosing apparatus according to Embodiment 1 in that outputs from driving circuits D1B to D6B are binary of zero to positive. For this reason, among the trigger signal line group TG through which trigger pulses are supplied from the transmission trigger generator 2, only one trigger signal line is connected to each of the driving circuits D1B to D6B.

Figure 28A:
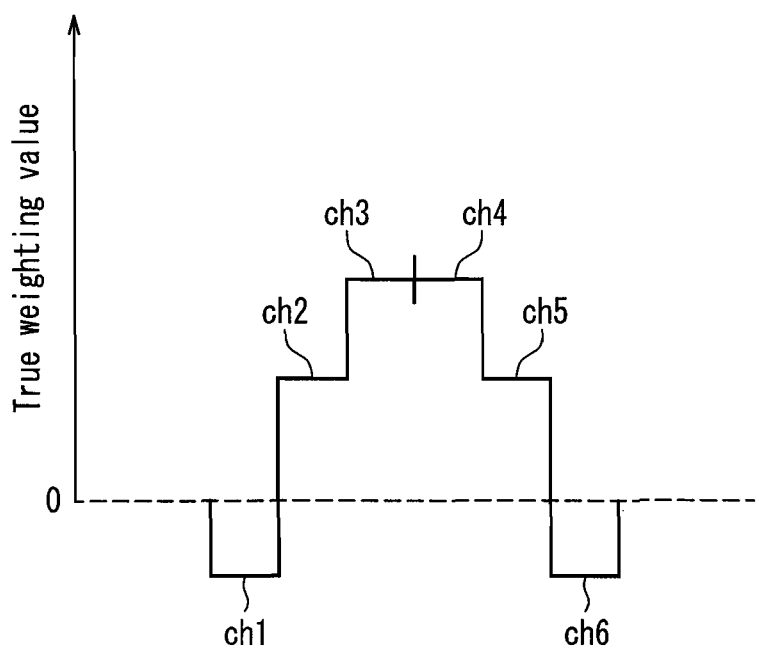
FIG. 28A is a diagram showing an example of weighting values in the ultrasonic diagnosing apparatus.

The operation of the ultrasonic diagnosing apparatus configured as above will be described with reference to FIGS. 27 to 29. First, FIG. 28A shows true weighting values assigned to outputs from the transducer elements T1 to T6. While the true weighting values corresponding to the transducer elements T2 to T5 are positive, the true weighting values corresponding to the transducer elements T1 and T6 are negative. The "true weighting value" refers to a predetermined weighting value calculated from Formula (2), for example.

Figure 28B:
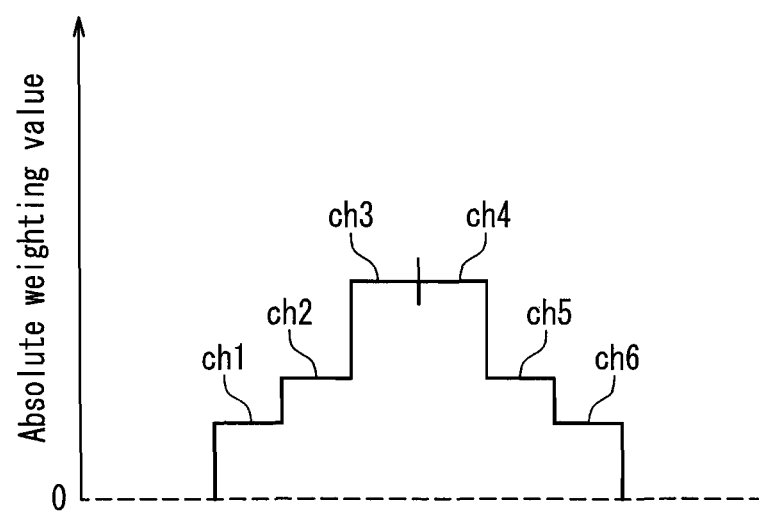
FIG. 28B is a diagram showing an example of weighting values in the ultrasonic diagnosing apparatus.

Outputs from the driving circuits D1B to D6B are binary of zero to positive so that they cannot be switched to negative. Thus, in this state, outputs corresponding to the true weighting values cannot be obtained from the transducer elements T1 and T6. To solve this problem, as shown in FIG. 28B, first, the output level of each of the driving circuits D1B to D6B is made proportional to an absolute weighting value corresponding to the absolute value of each true weighting value. In the example shown in FIG. 28B, since the absolute weighting values are positive, it is possible to handle this problem with the binary output driving circuits D1B to D6B. FIG. 29 shows an example of the binary output driving circuits D1B and B2B.

Figure 29:
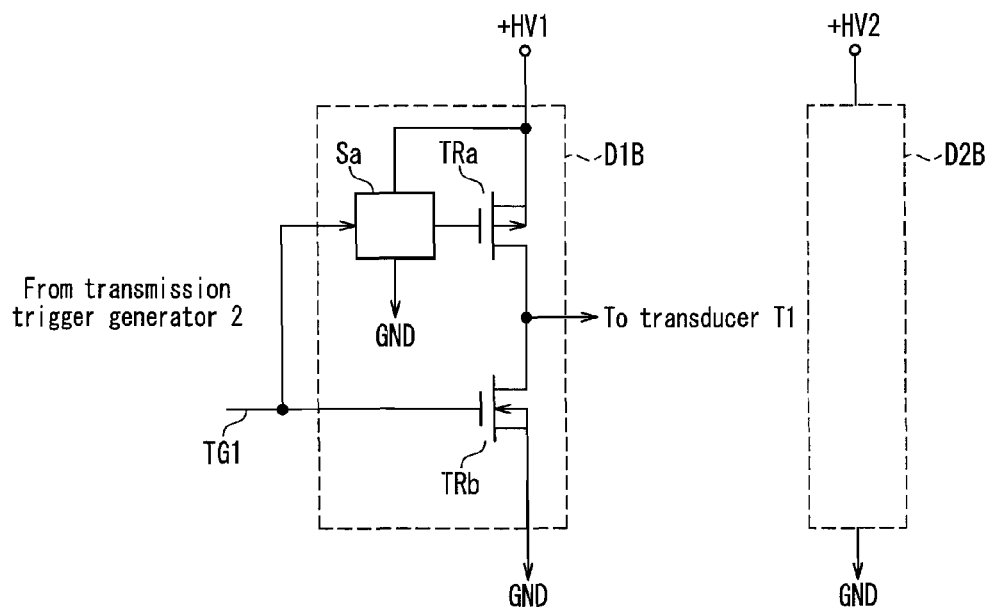
FIG. 29 is a block diagram showing a diving circuit of the ultrasonic diagnosing apparatus.

In FIG. 29, one trigger signal line of the trigger signal line group from the transmission trigger generator 2 is connected to the gates of the level shifter Sa and the NMOS transistor TRb to supply a trigger pulse TG1. An output of the level shifter Sa is supplied to the gate of the PMOS transistor TRa. The level shifter Sa shifts the level of output from the low-voltage transmission trigger generator 2 so that the output becomes suited for the high-voltage PMOS transistor TRa.

The source of the PMOS transistor TRa is connected to a positive power supply +HV1 and the source of the NMOS transistor TRb is connected to GND. The drains of the PMOS transistor TRa and the NMOS transistor TRb are connected to each other and are connected to the transducer T1. The driving circuit D2B is connected to a positive power supply +HV2 different from the positive power supply +HV1. In this way, the driving circuits D1B to D6B are connected respectively to the positive power supplies +HV1 to +HV6. The voltage value of each of the positive power supplies +HV1 to +HV6 is proportional to each absolute weighting value.

Figure 30:
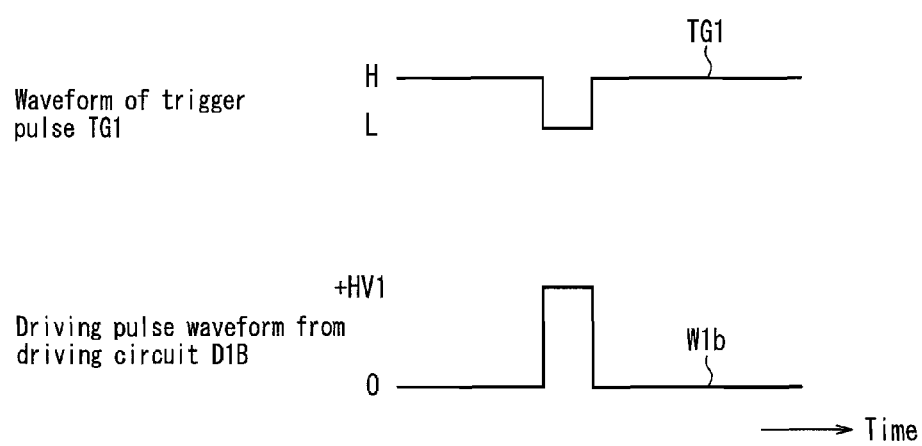
FIG. 30 is a diagram showing a trigger pulse inputted to a driving circuit of the ultrasonic diagnosing apparatus and a diving pulse waveform outputted from the driving circuit.

FIG. 30 shows the relationship between the waveform of the trigger pulse TG1 supplied to the gates of the level shifter Sa and the NMOS transistor TRb and a driving pulse W1b outputted from the driving circuit D1B.

In FIG. 30, when the trigger pulse TG1 is in H, the PMOS transistor TRa is off, the NMOS transistor TRb is on and the output of the driving circuit D1B is 0. Next, when the trigger pulse TG1 becomes L, the PMOS transistor TRa is turned on, the NMOS transistor TRb is turned off and the output of the driving circuit D1B becomes substantially +HV1. Further, when the trigger pulse TG1 returns to H, the PMOS transistor TRa is turned off and the NMOS transistor TRb is turned on and the output of the driving circuit D1B becomes 0.

The operations of the driving circuits D2B to D6B are also similar. In this way, the driving circuits D1B to D6B can generate binary driving pulses whose output levels correspond to the positive power supplies HV1 to HV6. The driving pulses may be binary outputs of 0 to negative. Each output level of the driving circuits D1B to D6B can also be controlled by controlling the pulse width of each trigger pulse to control the pulse width of each output of the driving circuits D1B to D6B.

Figure 31:
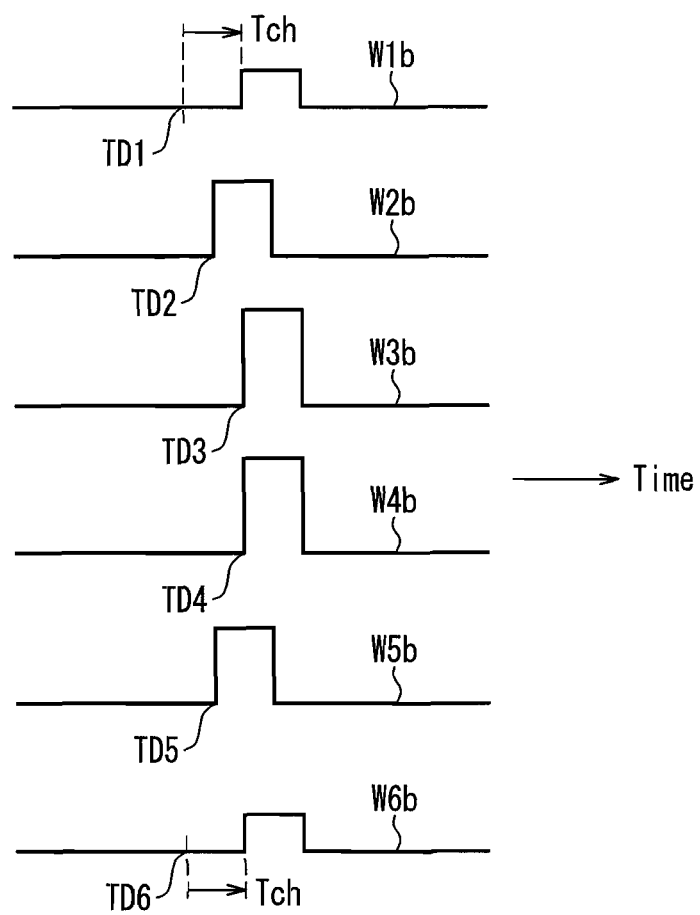
FIG. 31 is a diagram showing driving pulse waveforms outputted from the driving circuits of the ultrasonic diagnosing apparatus.
Figure 32:
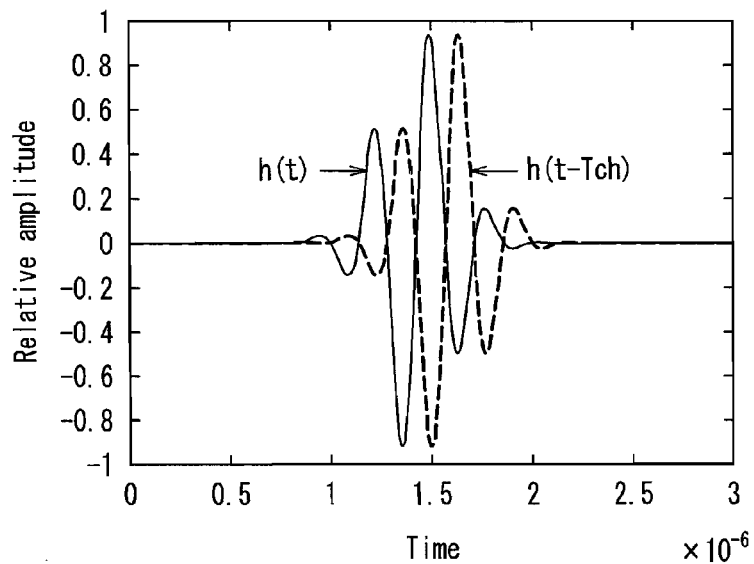
FIG. 32 is a diagram showing an example of an impulse response of a subsystem of the ultrasonic diagnosing apparatus.

FIG. 31 shows relationships among delay times of the driving pulses W1b to W6b outputted from the driving circuits D1B to D6B. As shown in FIG. 31, among delay times TD1 to TD6 of the driving pulses W1b to W6b, with respect to channels ch. 1 and ch. 6 where the true weighting values are negative, the delay times TD1 and TD6 are shifted by time Tch. Here, the time Tch corresponds to a half cycle of the transmission frequency of the transducer array 1. Ultrasound emitted from the transducer array 1 is a relatively-narrow-band pulse. Thus, as shown in FIG. 32, with a pulse h (t-Tch) obtained by delaying a pulse h (t) by the time Tch, it is possible to approximate a pulse inverted from the polarity of the pulse h(t).

Figure 33:
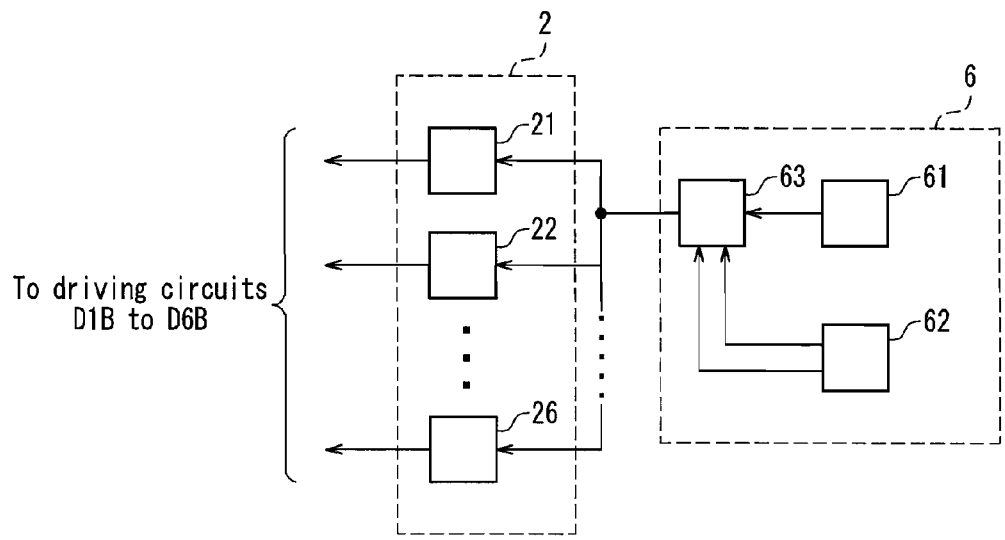
FIG. 33 is a block diagram showing a control unit of the ultrasonic diagnosing apparatus.

FIG. 33 shows an example of a circuit for changing transmission delay data. Among the components of this circuit, delay pulse generators 21 to 26 are included in the transmission trigger generator 2 and a delay data generator 61, a delay data compensator 62 and an adder 63 are included in the control circuit 6.

The delay data generator 61 generates delay data for converging transmission beams. The delay data compensator 62 generates a polarity sign of true delay data and the time Tch. When the sign of the delay data generated by the delay data compensator 62 is positive, the adder 63 does not change the corresponding delay data. On the other hand, when the sign of the delay data generated by the delay data compensator 62 is negative, the adder 63 changes the corresponding delay data by adding the time Tch to the delay data.

The adjusted delay data outputted from the adder 63 is supplied to the delay pulse generators 21 to 26. On the basis of the adjusted delay data, the delay pulse generators 21 to 26 generate trigger pulses and supply them to the driving circuits D1B to D6B.

Figure 34:
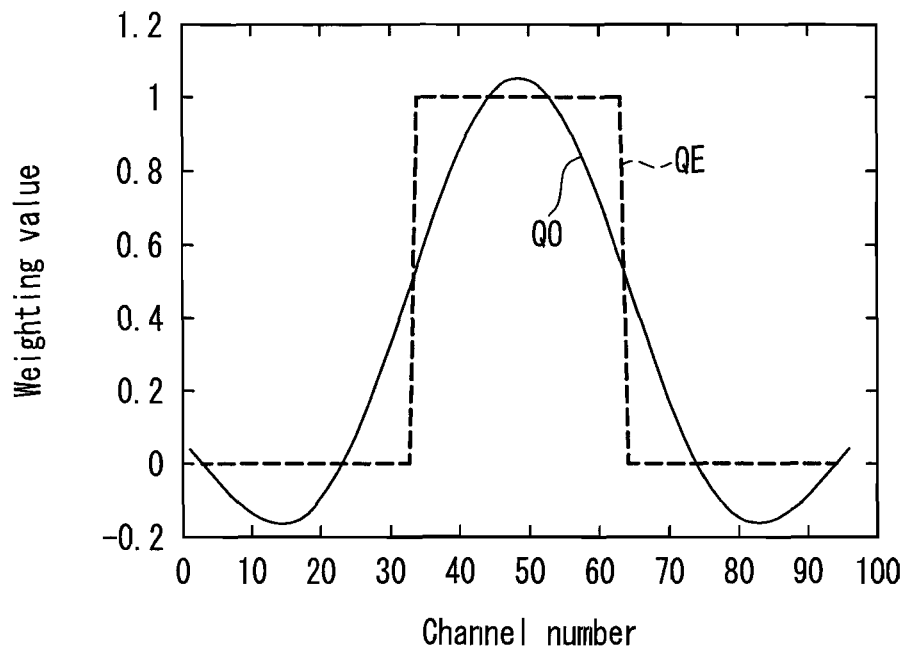
FIG. 34 is a diagram showing an example of transmission aperture weighting values of the ultrasonic diagnosing apparatus.

FIGS. 34 to 37 are diagrams showing the absolute weighting values and effects of shifting of driving pulse timings. FIG. 34 shows an example of transmission weighting values assigned to a transmission aperture with 96 channels. In FIG. 34, a solid line Q0 indicates true weighting values composed of positive and negative values. A broken line QE indicates values obtained by quantizing the absolute value of each true weighting value by a quantization unit 1. The weighting value of the channel at the center of the transmission aperture is 1.

Figure 35:
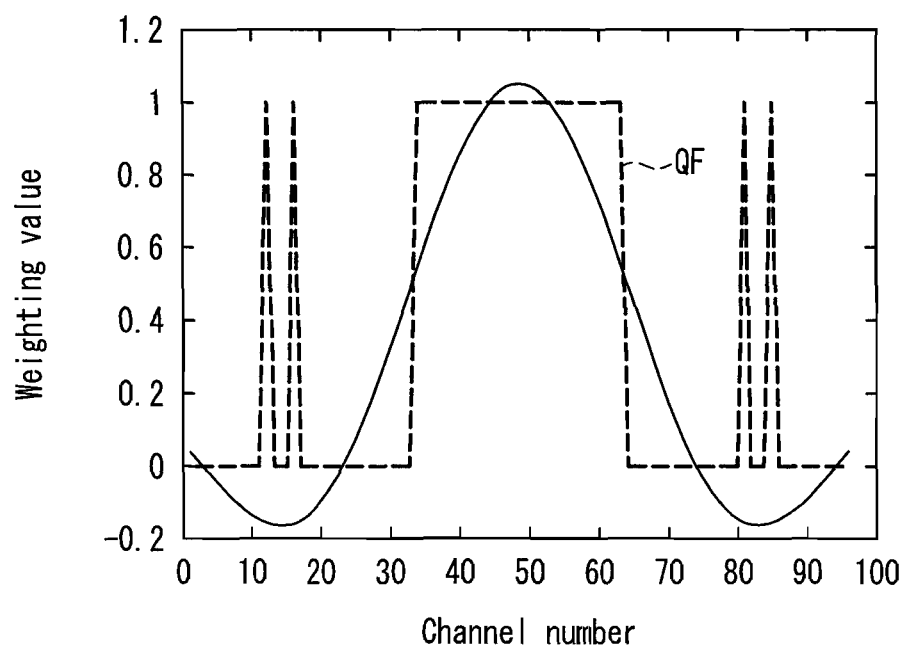
FIG. 35 is a diagram showing an example of transmission aperture weighting values of the ultrasonic diagnosing apparatus.

A broken line QF in FIG. 35 indicates a case where, among the channels where the quantized absolute weighting values in FIG. 34 become 0, the weighting values at channels 12, 16, 81 and 85 are changed to the minimum quantization unit 1. In the case of FIG. 35, all of the power supplies for the driving circuits can be of the same value. Furthermore, delay time in each of channels 12, 16, 81 and 85 is shifted by Tch.

Figure 36:
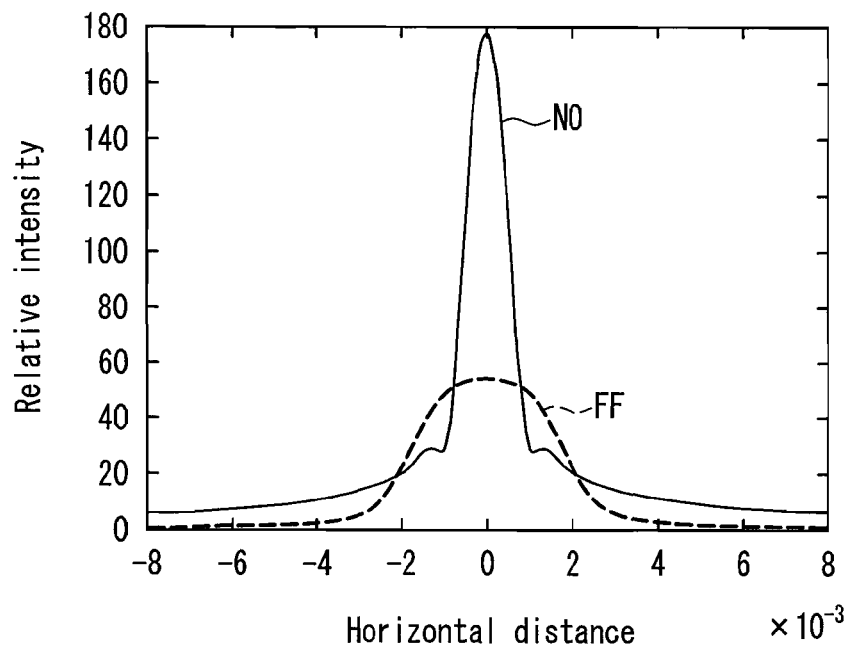
FIG. 36 is a diagram showing an example of beam shapes of the ultrasonic diagnosing apparatus.

A broken line FF in FIG. 36 indicates the shape of a cross-sectional intensity distribution on the focal plane of a transmission beam obtained in the case indicated by the broken line QF in FIG. 35, where a trapezoidal transmission beam is obtained. Further, a half width bw1 of the beam is wider than a half width bw2 of a transmission beam in the case without weighting indicated by a solid line N0, meaning that the beam is suited for parallel reception.

Figure 37:
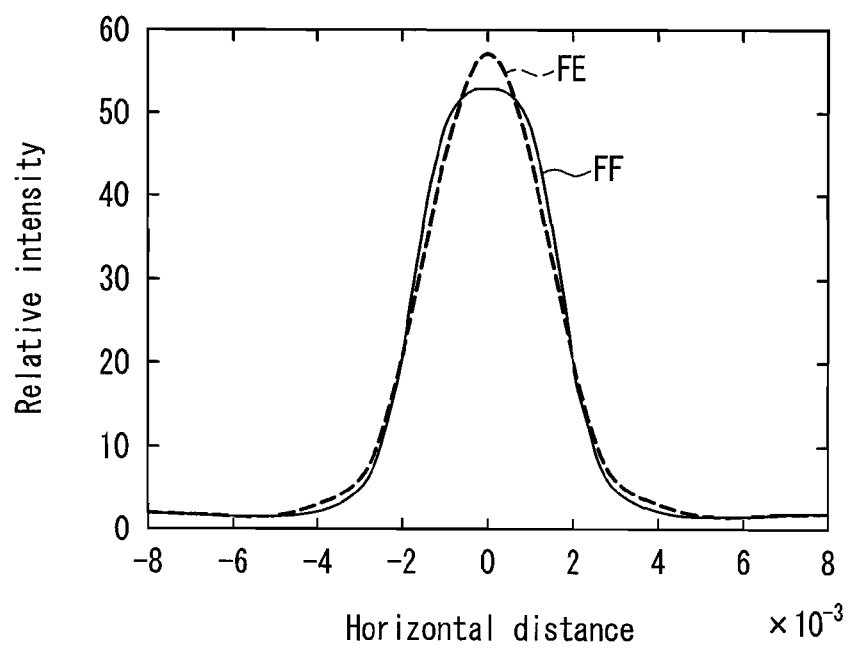
FIG. 37 is a diagram showing an example of beam shapes of the ultrasonic diagnosing apparatus.
Figure 38:
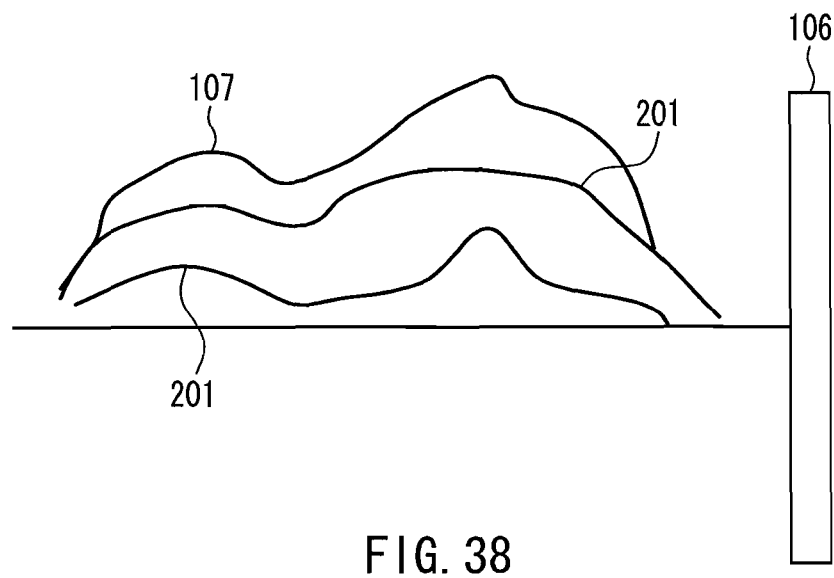
FIG. 38 is a diagram showing waveforms emitted from transducer elements of a conventional ultrasonic diagnosing apparatus.
Figure 39:
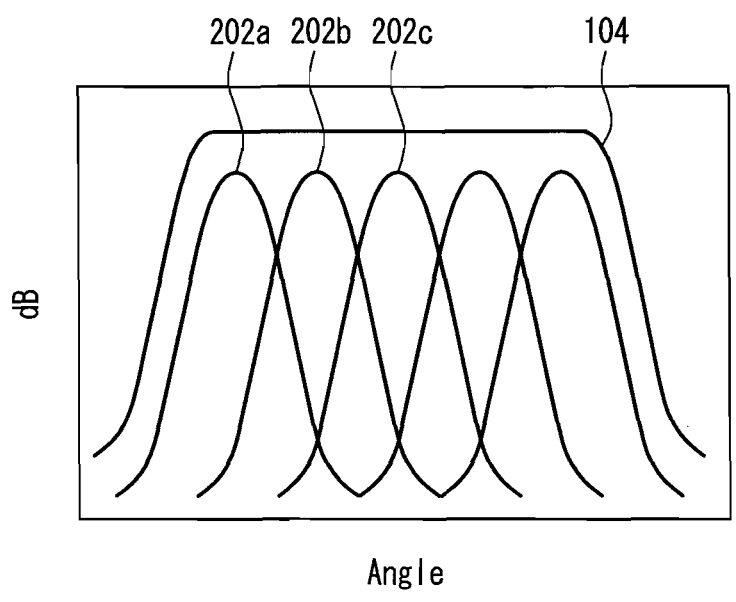
FIG. 39 is a diagram showing beam shapes of the conventional ultrasonic diagnosing apparatus.

FIG. 37 shows a comparison between a transmission beam shape obtained by using the absolute weighting values indicated by the broken line QE in FIG. 34 and a transmission beam shape obtained by using the absolute weighting values indicated by the broken line QF in FIG. 35. The transmission beam shape corresponding to the absolute weighting values indicated by the broken line QE is indicated by a broken line FE and the transmission beam shape corresponding to the absolute weighting values indicated by the broken line QF is indicted by a solid line FE As can be seen, the case indicated by the broken line QF in FIG. 35 where the weighting values are changed by the minimum quantization unit and delay time is shifted by Tch results in a transmission beam closer to a trapezoidal transmission beam suited for parallel reception.

Although the quantization unit in the above description has been 1, the shape of a trapezoidal transmission beam is improved by selecting a smaller value as the quantization unit. As examples of true weighting values, with which the intensity distribution of an ultrasound beam generated by the transducer array has a small fluctuation in the depth direction, and the cross-sectional intensity distribution of the ultrasound beam is formed to be trapezoidal so as to be suitable for parallel reception, there have been known a SIN C function when the transmission aperture formed by the transducer array is rectangular and a Bessel function when the aperture is circular.

As described above, according to the ultrasonic diagnosing apparatus according to the present embodiment, for true weighting values composed of positive and negative values, the output amplitudes of the driving circuits are controlled using the absolute weighting values and, on the basis of the polarity sign of each true weighting value, delay time of each driving circuit is shifted by the time Tch corresponding to a half cycle of the transmission frequency. As a result, it is possible to form a trapezoidal transmission beam and a rate at which data is acquired can be increased easily by using a plurality of reception beams.

INDUSTRIAL APPLICABILITY

According to the ultrasonic diagnosing apparatus of the present invention, a circuit that forms a trapezoidal transmission beam can be configured at low cost by using pulse amplifiers, so that it is useful as an apparatus using a plurality of parallel reception beams to improve a data acquisition rate.

The invention claimed is:

1. An ultrasonic diagnosing apparatus comprising:
   a transducer array composed of a plurality of arrayed transducer elements for transmitting ultrasound;
   a plurality of driving circuits each provided for transmission channels for driving each of the transducer elements;
   a transmission trigger generator for generating a trigger pulse for controlling each of the driving circuits;
   a parallel reception beam former for processing reception signals from the transducer elements; and
   a signal processor for processing an output signal of the parallel reception beam former,
   wherein the transmission trigger generator controls a width of the trigger pulse independently for each of the transmission channels to cause the driving circuit to output a driving pulse approximating a predetermined weighting value assigned to an output amplitude of each of the transmission channels in a transmission aperture of the transducer array.

2. The ultrasonic diagnosing apparatus according to claim 1, wherein in comparison to the trigger pulses inputted to the driving circuits for the transmission channels corresponding to a center portion and peripheral portions of the transmission aperture of the transducer array, the trigger pulses inputted to the driving circuits for the transmission channels corresponding to intermediate areas between the center portion and the peripheral portions have a narrower width.

3. The ultrasonic diagnosing apparatus according to claim 1, wherein the weighting to the output amplitude of each of the transmission channels is controlled by controlling independently for each of the transmission channels the number of cycles of the trigger pulse inputted to the driving circuit.

4. The ultrasonic diagnosing apparatus according to claim 1, wherein the weighting to the output amplitude of each of the transmission channels is controlled by controlling independently for each of the transmission channels a time phase of the trigger pulse inputted to the driving circuit to be inverted.

5. The ultrasonic diagnosing apparatus according to claim 4, wherein the plurality of transducer elements of the transducer array are divided into three groups when being driven, and with respect to a time phase of the trigger pulses inputted to the driving circuits for a group at a center of the transmission aperture, a time phase of the trigger pulses inputted to the driving circuits for peripheral groups on both sides of the center group is inverted.

6. The ultrasonic diagnosing apparatus according to claim 1, wherein the driving circuits are ternary output driving circuits, and the weighting value is approximated by controlling independently for each of the transmission channels at least one of the width, the number of cycles and the time phase of the trigger pulse.

7. The ultrasonic diagnosing apparatus according to claim 1, wherein with respect to a relative coordinate X measured from a center of the array of the transducer array as a starting point, the predetermined weighting value w (X) is assigned by the following formula:

$$w(X) = \mathrm{SIN}\, C(2 \times) + C$$

where $-1 \leq X \leq 1$ and $0.02 \leq C \leq 0.08$.

8. The ultrasonic diagnosing apparatus according to claim 7, wherein the weighting value w (X) is discretized by a quantization unit value q (where $\frac{1}{8} \leq q \leq 1$).

9. The ultrasonic diagnosing apparatus according to claim 8, wherein when the discretized weighting value becomes 0 over a plurality of adjacent transmission channels, for some of the adjacent transmission channels where the weighting value becomes 0, the weighting value is changed by the quantization unit value as a minimum unit.

10. The ultrasonic diagnosing apparatus according to claim 8, wherein intervals between discritizations of the predetermined weighting value are set to be longer as an ultrasound transmission frequency becomes higher.

11. The ultrasonic diagnosing apparatus according to claim 1, wherein a timing of the driving pulse is shifted by an amount of time corresponding to a ½ cycle when a polarity of the predetermined weighting value is positive with respect to a case where the polarity is negative.

12. The ultrasonic diagnosing apparatus according to claim 11, wherein the driving circuits are binary output driving circuits.

13. The ultrasonic diagnosing apparatus according to claim 11, wherein time amount data corresponding to a ½ cycle is added to or subtracted from delay data for specifying the timing of the driving pulse in accordance with the polarity of the predetermined weighting value.

14. The ultrasonic diagnosing apparatus according to claim 11, wherein an output of each of the transmission channels is controlled in accordance with an absolute weighting value corresponding to an absolute value of the predetermined weighting value.

15. The ultrasonic diagnosing apparatus according to claim 11, wherein an absolute value of the predetermined weighting value is quantized, and for some of the transmission channels where the quantized absolute weighting value becomes 0, the absolute weighting value is changed by a minimum quantization unit.

16. The ultrasonic diagnosing apparatus according to claim 1, wherein the transmission trigger generator controls the output amplitude based on a generation interval of the trigger pulse.

* * * * *

UNITED STATES PATENT AND TRADEMARK OFFICE
CERTIFICATE OF CORRECTION

| | |
|---|---|
| PATENT NO. | : 8,444,561 B2 |
| APPLICATION NO. | : 12/810748 |
| DATED | : May 21, 2013 |
| INVENTOR(S) | : Fukukita et al. |

Page 1 of 1

It is certified that error appears in the above-identified patent and that said Letters Patent is hereby corrected as shown below:

On the Title Page, Item (22) PCT Filed: delete "Dec. 25, 2008" and insert --Dec. 22, 2008--.

Signed and Sealed this
Thirtieth Day of July, 2013

Teresa Stanek Rea
*Acting Director of the United States Patent and Trademark Office*